(12) United States Patent
Larimer et al.

(10) Patent No.: US 10,005,999 B2
(45) Date of Patent: Jun. 26, 2018

(54) METHOD AND APPARATUS FOR MEASURING BIOFILM THICKNESS AND TOPOLOGY

(71) Applicant: BATTELLE MEMORIAL INSTITUTE, Richland, WA (US)

(72) Inventors: Curtis J. Larimer, Richland, WA (US); Jonathan D. Suter, Richland, WA (US); Raymond S. Addleman, Benton City, WA (US); George T. Bonheyo, Sequim, WA (US); Michelle R. Brann, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 58 days.

(21) Appl. No.: 15/071,921

(22) Filed: Mar. 16, 2016

(65) Prior Publication Data
US 2016/0272933 A1 Sep. 22, 2016

Related U.S. Application Data

(60) Provisional application No. 62/134,945, filed on Mar. 18, 2015.

(51) Int. Cl.
| | |
|---|---|
| C12M 1/00 | (2006.01) |
| C12M 1/34 | (2006.01) |
| C12M 1/32 | (2006.01) |
| C12M 1/36 | (2006.01) |
| G01B 9/02 | (2006.01) |
| G01B 11/06 | (2006.01) |
| G01B 11/24 | (2006.01) |

(52) U.S. Cl.
CPC ............ *C12M 41/46* (2013.01); *C12M 23/12* (2013.01); *C12M 23/22* (2013.01); *C12M 23/58* (2013.01); *C12M 29/10* (2013.01); *C12M 41/36* (2013.01); *C12M 41/48* (2013.01); *G01B 9/0209* (2013.01); *G01B 9/02021* (2013.01); *G01B 11/0675* (2013.01); *G01B 11/2441* (2013.01)

(58) Field of Classification Search
CPC ...... C12M 41/36; C12M 21/06; C12M 23/16; C12M 35/04; C12M 23/12; C12M 29/10; C12M 23/22; C12M 23/44; C12M 23/58; C12M 33/12; C12M 41/46; C12M 41/48; B01L 2200/025; B01L 2200/027; B01L 2200/0647; B01L 2200/00; A01N 63/00; A61L 2300/64; A61L 2430/02; A61L 27/446; A61L 27/54; A61L 27/56; A61L 2300/252; A61L 2300/406; A61L 2300/41; A61L 2300/44; A61L 27/16; A61L 27/18; A61L 27/20; A61L 27/3834; A61L 27/3847
See application file for complete search history.

(56) References Cited

U.S. PATENT DOCUMENTS

| | | | |
|---|---|---|---|
| 5,317,389 A | 5/1994 | Hochberg et al. | |
| 6,140,116 A | 10/2000 | Dinsmore | |
| 7,119,909 B2 | 10/2006 | Unruh et al. | |
| 7,466,429 B2 | 12/2008 | De Groot et al. | |
| 7,612,891 B2 | 11/2009 | Wan | |
| 7,755,768 B2 | 7/2010 | Mansfield | |
| 8,293,524 B2 * | 10/2012 | Ionescu-Zanetti | B01L 3/502715 435/287.1 |
| 8,553,231 B2 | 10/2013 | Medicus et al. | |

FOREIGN PATENT DOCUMENTS

| | | |
|---|---|---|
| EP | 2482031 A1 | 8/2012 |
| WO | 2013019984 A1 | 2/2013 |

OTHER PUBLICATIONS

Invitation to Pay Additional Fees and, Where Applicable, Protest Fee and Communication Relating to the Results of the Partial International Search for International Application No. PCT/US2016/022818, International Filing Date Mar. 17, 2016, dated Jun. 24, 2016.
Li, X., et al., Full-field quantitative phase imaging by white-light interferometry with active phase stabilization and its application to biological samples, Optics Letters, 31, 12, Jun. 15, 2006, 1830-1832.
Anastasiadis, P., et al., Detection and quantification of bacterial biofilms combining high-frequency acoustic microscopy and targeted lipid microparticles, Journal of Nanobiotechnology, 12, 24, 2014, 1-11.
Reed, J., et al., Live Cell Interferometry Reveals Cellular Dynamism During Force Propagation, ACS Nano, 2, 5, 2008, 841-846.
Reed, J., et al., Mechanical Interferometry of Nanoscale Motion and Local Mechanical Properties of Living Zebrafish Embryos, ACS Nano, 3, 8, 2009, 2090-2094.
Reed, J., et al., Rapid, Massively Parallel Single-Cell Drug Response Measurements via Live Cell Interferometry, Biophysical Journal, 101, 2011, 1025-1031.

(Continued)

*Primary Examiner* — Debbie K Ware
(74) *Attorney, Agent, or Firm* — Derek H. Maughan

(57) ABSTRACT

An apparatus and method of measuring biofilm and biological activity on a surface is disclosed. The apparatus includes a biofilm, which includes one or more microorganisms, grown on a substrate. A viewing window is placed on a surface of the biofilm and a gas bubble is introduced between the viewing window and the surface of the biofilm. The space between the substrate and the viewing window may be enclosed in a casing that has an inlet and an outlet, forming a flow cell. A microscope system, such as a white light interferometer, captures data of the biofilm in situ and non-destructively. The 3D images of biofilm surface have high resolution while maintaining a large field of view. The apparatuses and methods will be useful for fundamental studies of biofilms, biomedical and environmental screening, and many other applications in biology and the life sciences.

4 Claims, 20 Drawing Sheets

(56) References Cited

OTHER PUBLICATIONS

Reed, J., et al., Interference microscopy offers new applications for biomedical research, SPIE, DOI: 10.1117/2.1201302.004707, 1-3.
Han, S., Interferometric Testing through Transmissive Media (TTM), Proc of SPIE vol. 6293, 1-5, 2006.
Schmit, J., et al., Performance advances in interferometric optical profilers for imaging and testing, J Opt A: Pur Appl Opt, 10, 2008, 1-7.
Reed, J., et al., High throuphput cell nanomechanics with mechanical imaging interferometry, Nanotechnology, 19, 2008, 1-8.
International Search Report/Written Opinion for International Application No. PCT/US2016/022818, International filing date Mar. 17, 2016, dated Aug. 17, 2016.

* cited by examiner

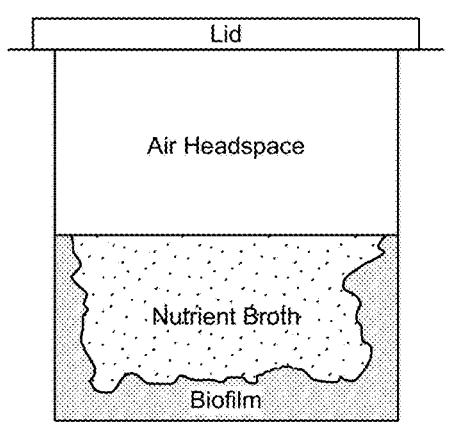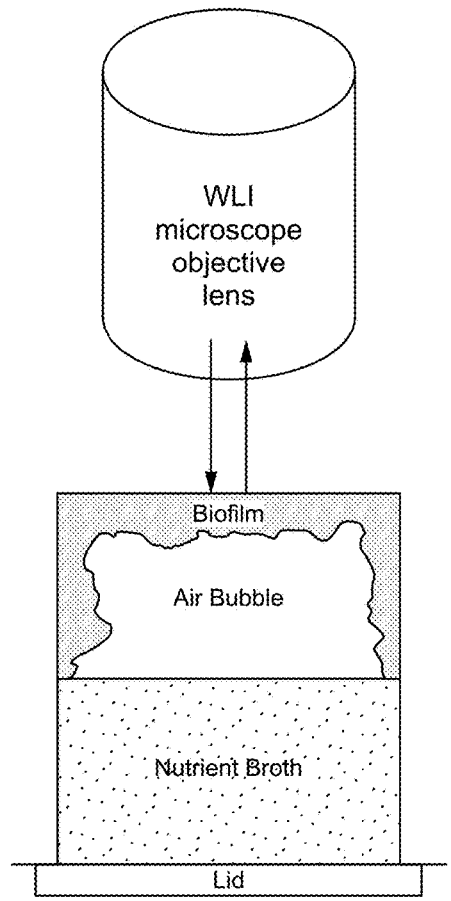
Fig. 14A                     Fig. 14B

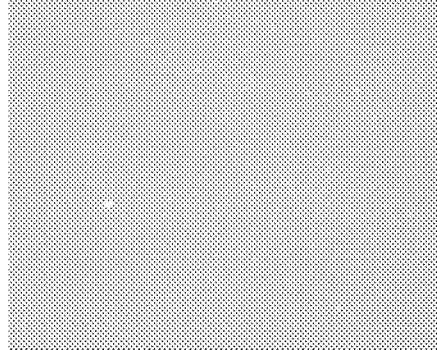
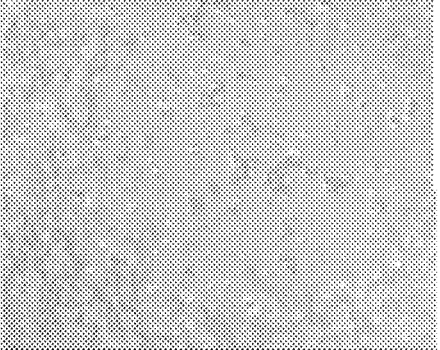
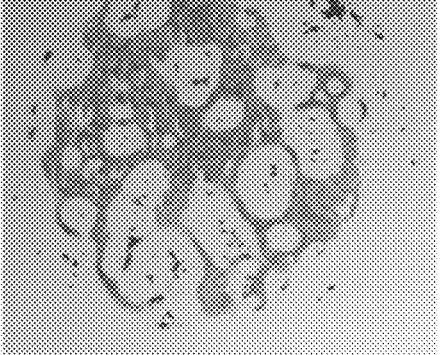
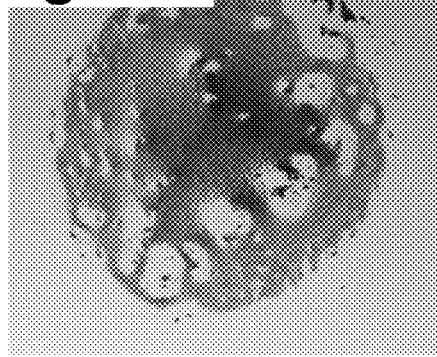
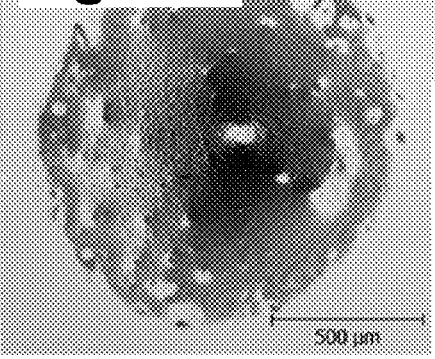
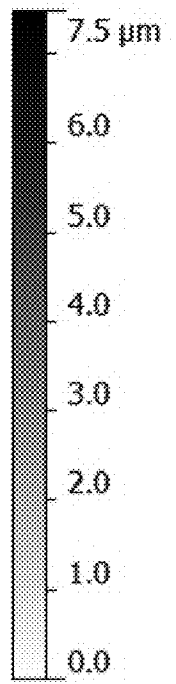

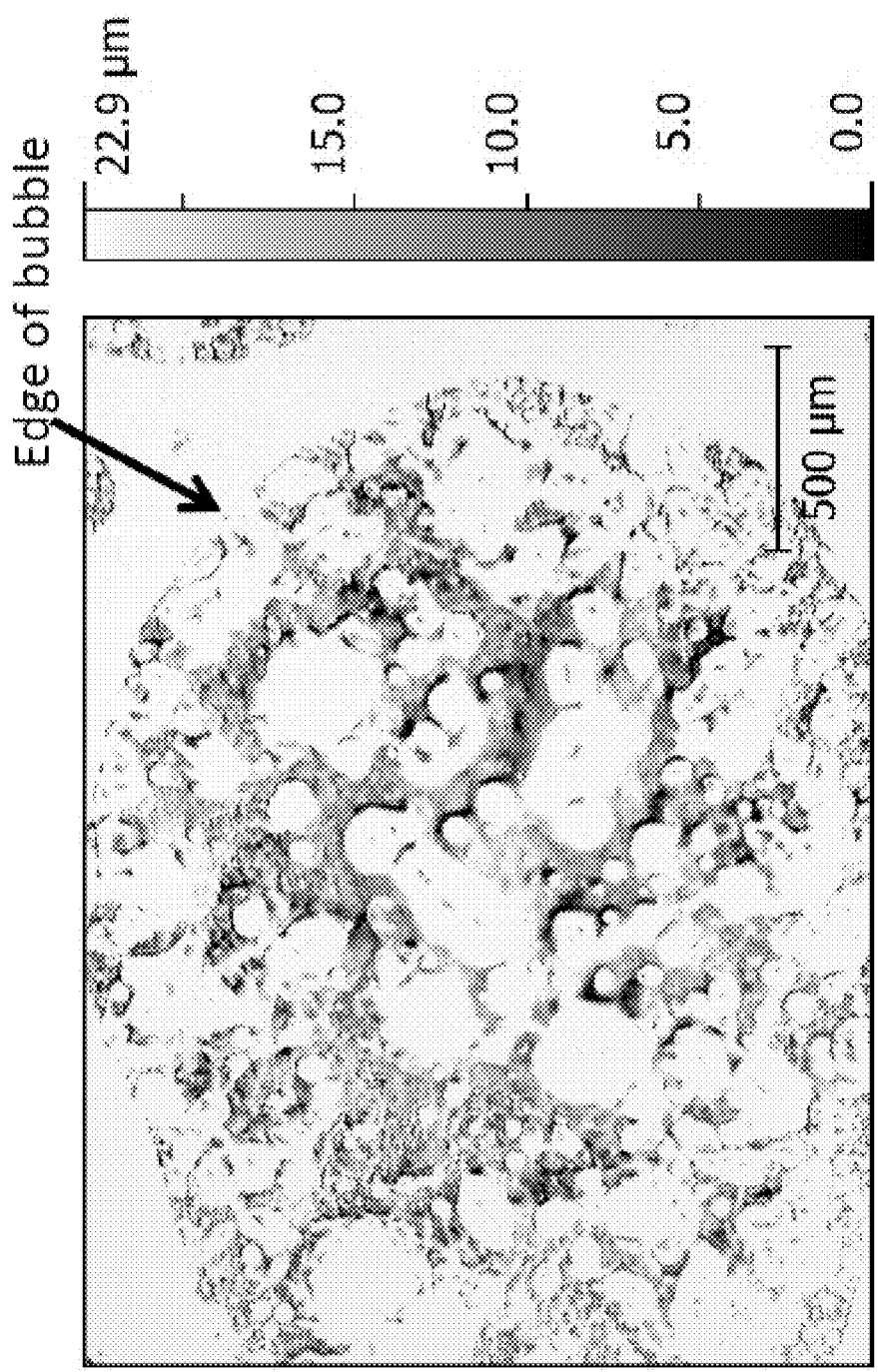

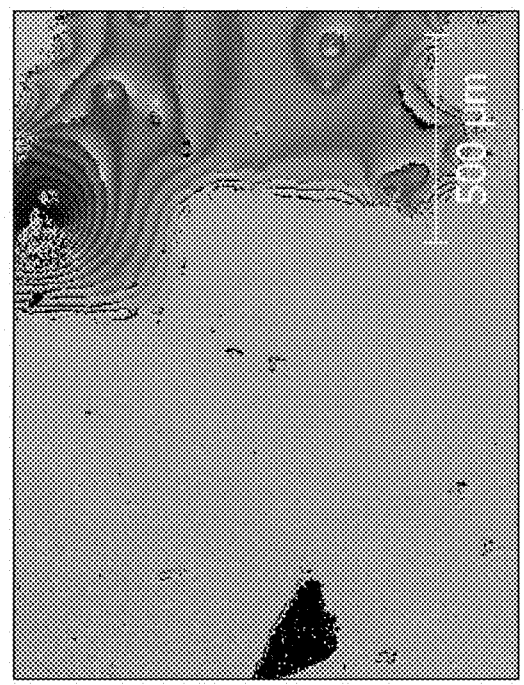
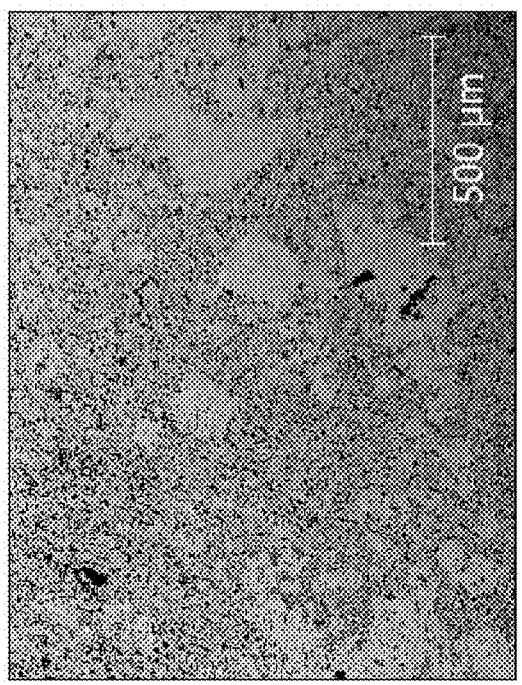
Fig. 20A
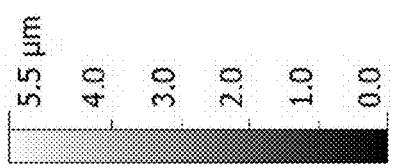
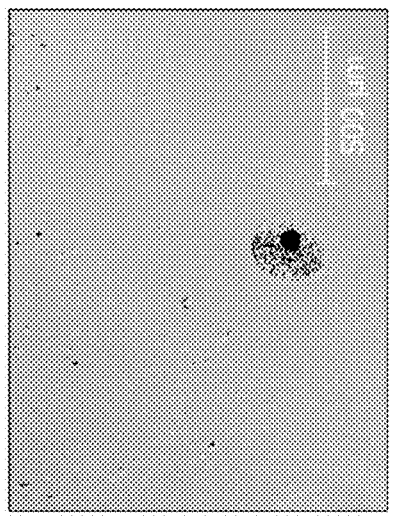
Fig. 20B
Fig. 20C

METHOD AND APPARATUS FOR MEASURING BIOFILM THICKNESS AND TOPOLOGY

CROSS-REFERENCE TO RELATED APPLICATIONS

This application claims priority to U.S. Provisional Application Ser. No. 62/134,945, filed Mar. 18, 2015, titled "METHOD AND APPARATUS FOR NON-DESTRUCTIVE EVALUATION OF BACTERIAL BIOFILMS WITH WHITE LIGHT INTERFEROMETRY," hereby incorporated by reference in its entirety for all of its teachings.

STATEMENT REGARDING FEDERALLY SPONSORED RESEARCH OR DEVELOPMENT

This invention was made with Government support under Contract DE-AC0576RL01830 awarded by the U.S. Department of Energy. The Government has certain rights in the invention.

TECHNICAL FIELD

This invention relates to biofilms. More specifically, this invention relates to a non-destructive high resolution method of measuring and monitoring the thickness and/or topology of live biofilms using white light interferometric optical microscopy.

BACKGROUND

The structured communities of environmental bacteria known as biofilms are pervasive in wet environments. Biofilms can be essential components in natural processes but can also be disruptive to industrial systems, be the source of harmful medical and dental health issues, cause environmental problems such as transporting invasive species, and decrease the fuel efficiency of ocean going vessels. The ability to measure biofilms is essential for understanding and addressing associated issues. When fully hydrated, the bulk properties of biofilms can be very similar to those of water, making it difficult to delineate the barrier between the biofilm and the surrounding bulk liquid.

Reliable and repeatable methods to observe biofilm structure and properties in three dimensions are needed in order to improve our fundamental understanding and to provide a platform to study new materials and treatments that may be used to prevent biofilm growth. Historically, microscopy has played an important role in the discovery and understanding of microbes. In situ imaging techniques are highly desirable because biofilms can vary significantly from sample to sample. Statistical averages from repeated experiments offer poor measurement resolution and large standard deviations. If instead a biofilm could be investigated non-destructively, its structure could be observed over time—during colonization or while an intervention is applied, for example.

New chemicals and drugs are needed to mediate the negative effects of biofilms. However, non-destructive tools to screen new treatments lack key abilities to study biofilms with high spatial and temporal resolution.

A common technique for 3D imaging of biological samples is confocal scanning laser microscopy (CLSM) in combination with fluorescent staining. This type of microscopy has the advantage of providing axial (vertical) information in addition to lateral (horizontal). This is accomplished by collecting data from a scanned array of points in a series of vertically separated planes. Confocal microscopy can be used to reconstruct 3D images of bacterial biofilms. Observing the "edge" or "surface" of the biofilm is not done directly; rather, the data cube is analyzed and a threshold is algorithmically determined to estimate the position of the edge. There are two major limitations of this approach with respect to the ability to use this data to study surface topology of biofilms. Namely, confocal microscopy is necessarily limited to a relatively small field of view (especially if high axial or lateral resolution is desired) and the indirect nature of the surface measurement adds uncertainty to the measurement.

Similarly, electron microscopy (scanning or transmission) and atomic force microscopy (AFM) are limited by relatively small field of view and typically require exposure of the sample to destructive environments. In the case of SEM or TEM, bacteria must also be killed, fixed, desiccated and exposed to high vacuum. In AFM, it is possible to measure wet samples, though desiccation is required for optimal resolution, and contact with a stylus is always required.

Optical techniques for studying biofilms are of particular interest because they are non-destructive and capable of real-time or near real-time in situ measurements. Light and epifluorescence microscopy are often paired with specific staining of microbiological samples. While simple and fast, light microscopy is also limited by low resolution and narrow depth of field. Low resolution is particularly apparent in the axial (vertical) dimension because it is constrained by the depth of field of the objective lens.

The field of view that can be seen by common biofilm imaging techniques narrows as higher magnification lenses are used to increase resolving power of the system. The high resolution necessary to resolve individual bacteria (>~400× magnification) may limit the field of view (<450 μm) such that it can be difficult to observe medium or large scale features (e.g., thickness and surface roughness) that are key features in understanding biofilms. Often, the high magnification needed to image individual cells requires very low working distance or even contact with the biofilm, which fundamentally alters the biofilm's natural structure.

Optical coherence tomography (OCT) is a prominent 3-D biomedical imaging technique that is based on low-coherence interferometry. OCT typically employs near-infrared light that can penetrate shallowly into soft tissue samples. It is similar in function to ultrasound imaging, but has higher resolution owing to the use of a broad band light source. Light reflected from near surface features of a sample interferes with light directed at a reference arm. However, OCT is limited to micrometer vertical resolution by the long wavelength of the light source. OCT is well-suited for applications where light must penetrate the surface such as in ophthalmology.

White light interferometry (WLI) is a specialized technique designed to measure surface profiles over large areas with high precision. WLI is typically used for surface metrology of solids. The technique is similar to OCT in that it is based on low-coherence interferometry. However, in WLI light reflects from the sample surface and does not penetrate it because low wavelength light is used rather than near-infrared. WLI instruments are designed to measure the 3-dimensional profile of a relatively large area of a sample. Lateral resolution is unchanged from traditional light microscopy (i.e. limited by the diffraction) but the vertical resolution is extremely fine.

A comparison of microscopic imaging techniques is shown in Table 1. The table compares lateral resolution, vertical resolution and field of view for each type of microscopy. WLI is unique in this list owing to the extremely fine vertical resolution and the ability to maintain this high resolution when imaging a large field of view. WLI has potential to vastly improve both the vertical resolution and the size of a biofilm sample that can be imaged in a single field of view.

TABLE 1

Resolution and field of view of common biofilm imaging techniques

| Method | Lateral resolution | Vertical Resolution | Field of View | Notes |
| --- | --- | --- | --- | --- |
| White light interferometry | 3.7 μm | 3 nm | 2-6 mm | Reflective surface required |
| Optical microscopy | ~400 nm | ~400 nm | <450 μm | Narrow depth of field and small field of view |
| Optical Coherence Tomography | 4 μm | 3 μm | 2.9 mm | Low resolution |
| Confocal microscopy | ~250 nm limit | 3 nm | <450 μm | Obtaining large field of view requires scanning/stitching |
| CLSM | ~150 nm limit | 400 nm | <450 μm | Thin sample required, small field of view, poor vertical resolution |
| Fluorescence microscopy | ~250 nm limit | 400 nm | <450 μm | Sample must be fluorescent or labeled |
| Fluorescence super-resolution microscopy | ~30 nm | <100 nm | 1-2 μm | Sample must be fluorescent or labeled |
| Photoacoustic spectroscopy | 100-200 μm | 10 μm | 150 μm | Sample exposed to air, low resolution |
| Ultrasonic imaging | ~50 μm | 15 μm | >1 mm (scanning) | Can't resolve low acoustic impedance differences |
| AFM (liquid) | <10 nm | <1 nm | ~10 μm | Requires contact, weakly bound samples lower resolution, small field of view |
| Environmental SEM | 1-20 nm | ~1 nm | ~12 μm for high resolution | Destructive sample preparation |

WLI is capable of high vertical resolution because it uses interferometry to measure the distance from the objective lens to the sample. In a typical WLI microscope a source of white light (e.g., a light emitting diode) is aimed at a beam splitter. Part of the beam is directed to the sample while the remainder is reflected off of a smooth reference mirror. The reflected light from these two surfaces recombine on the imaging detector and create interference fringes when the optical path length of the experimental and reference beams are nearly equal. In some interferometric objective lenses the mirror is positioned differently than the standard Michelson-type configuration (called a Mirau objective), but the principle and the effect are the same.

When operated in vertical scanning mode, the objective is lowered through a user-defined vertical range. Fringes of light intensity appear in the image whenever a reflective surface in the sample is at an optical path distance equal to the distance to the reference mirror. The time at which fringes appear during the vertical scan indicates the height of the sample surface features. With WLI, vertical resolution far exceeds the Rayleigh criterion because it is easy to observe small differences in optical path through subtle shifts in the interference fringes. In vertical scanning mode differences in vertical height as low as 3 nm can be observed. WLI is does not suffer $2\pi$ ambiguity that occurs with high coherence sources like lasers. The short fringe packet produced by white light can be assigned to an absolute height value.

WLI has rarely been used to measure soft surfaces of living organisms or cells or specifically for biofilms. The primary reason for this is that biofilms grow in aqueous environments. Water complicates WLI measurements because its increased refractive index relative to air leads to a shift in optical path length of light passing through it. Biofilm has a refractive index that is almost equal to water because much of a biofilm's volume is composed of water. As a result, a biofilm's surface will generally not reflect light. To resolve a surface or interface on an interferometric optical microscope the surface must be at least partially reflective. Non-reflective surfaces will not return enough light back to the microscope objective to generate measurable fringe contrast. For the same reason, samples or sample features with steep slopes will often not reflect in the direction of the objective lens and are not measurable. In these cases, the resulting profile image will have points or regions of missing or distorted data.

A limited number of previous studies have used WLI to measure the interface of wet biological samples. In these studies optical profiles were often collected from wet samples that were exposed to open air. Doing so for biofilms is not desirable because evaporation from the surface of the biofilm can significantly change its structure. In fact, evaporation can make imaging the liquid layer challenging because the interface must be stable and free of vibration/movement to produce interference in the reflected light.

WLI has also been used to measure the presence of cells by observing the shift they cause in optical path length. The presence of cells that are semi-transparent and of slightly different density than the surrounding water may lead to a slight change in refractive index and thus a slight change in optical path length. In this case, it is only possible to observe the presence of cells and their relative thickness. Absolute measurement of thickness is only possible if the refractive index of the cells is known in advance.

Measuring the thickness of a biofilm on a surface provides a means of assessing how much biomass has accumulated:

an important factor to consider when testing and evaluating strategies meant to inhibit biofilm formation. Unlike other methods (e.g., weight gain or extraction and determination of total organic carbon), WLI microscopy would allow a materials scientist to determine precisely where on a surface biomass is accumulating. For example, a corrosion engineer may want to examine if biofilms are forming in locations where crack, crevice, or galvanic corrosion occurs. Thickness is also roughly associated with the potential for anoxia at the base of the biofilm and with the diffusion of solutes into or out of a biofilm. The thickness of a biofilm is also critical to the function of percolating filters, membrane biofilm reactors, and other biofilm dependent strategies used in wastewater remediation. Biofilm cohesion and polysaccharide concentration increase with depth, not age in biofilms.

Additionally, the surface texture (roughness) of biofilms has an impact on fluid dynamics and with drag in particular. Topology and its effects on fluid dynamics also influence the diffusion of oxygen to the base of a biofilm. When studying biofilm growth on a textured surface, e.g., microtopography used in an attempt to alter hydrodynamics or to prevent biofouling, it may be informative to see whether the surface of the film follows the underlying topography of the substrate or if any other patterns of heterogeneity in the film are observed that correspond with preexisting patterns made in the substrate.

As described above there are many microscopy methods that can be used to study biofilms. Each method may also have a specific apparatus that positions the sample and provides suitable optical properties for imaging. Apparatuses that are designed for live biofilms must also support bacterial growth. No apparatus exists that can position a biofilm for WLI imaging and provide suitable optical conditions.

Two of the most common apparatuses for biofilm imaging are multi-well plates and flow cells. A multi-well plate is a flat plate with many "wells" that each can be used as small test tubes. Multi-well plates are a standard tool in analytical research and in diagnostic laboratories. Multi-well plates are also known as microplates or microtiter plates. Each plate may have 6, 12, 24, 48, 96, 384 or 1536 sample wells. The wells are arranged in a rectangle and are typically molded into a 5 inch by 3.33 inch plastic rectangle. The dimensions of the plate and each well are standardized for interoperability. Numerous instruments can be used to automatically fill each well with a desired analyte and complete analysis. A large market exists for robots that handle, transfer, store, analyze and clean multi-well plates. A common use for multi-well plates is in the enzyme-linked immunosorbent assay (ELISA), which is frequently used in medical diagnostic testing.

Specialty multi-well plates are manufactured for a specific assay or analytical method. Today, there are multi-well plates for many applications in life science research. There are plates for filtration, separation, storage, reaction mixing, detection of antimicrobial activity, cell culture, and optical detection. For example, multi-well plates are made with a flat glass bottom that is suited to microscopy or spectroscopy. Typically, when used for microscopy, the plate is placed bottom down on a microscope stage. The microscope must function in inverted configuration and "look up" at the bottom of each well.

Multi-well plates have been designed to study biofilms and antimicrobials that target biofilms. The plates used for this purpose can follow the Minimum Biofilm Eradication Concentration (MBEC) protocol and are referred to as MBEC plates or as a Calgary Biofilm Device. MBEC plates have a special lid with pegs designed to be partially submerged in wells that are inoculated with bacterial culture. The pegs then become coated in biofilm and can be removed for further analysis.

Flow cells are tools that are designed to study biofilms in dynamic conditions. Biofilms in the environment may encounter flowing liquid, depletion of nutrients, or toxic conditions. Flow cells provide an environment in which these variables and many others can be controlled and monitored. Flow cells typically have an experimental chamber with an inlet and an outlet. Liquid can enter and pass through the experimental chamber. Pumps are used to direct flow of liquid in these systems. When the flow cell is designed for microscopy the experimental chamber has a viewing window. The viewing window must have correct positioning and optical properties for the chosen microscopy technique.

What is needed to advance the study and prevention of bacterial biofilms is an apparatus and method for non-destructive, high resolution measurement and monitoring of biofilm thickness and topology.

SUMMARY

The present invention is directed to methods and apparatuses for measuring biofilm thickness and topology. In one embodiment, an apparatus for measuring biofilm thickness and topology is disclosed. The apparatus includes a biofilm including one or more microorganisms grown on a substrate. The apparatus further includes a viewing window placed on the surface of the biofilm. The apparatus also includes a gas bubble introduced between the viewing window and the surface of the biofilm.

In one embodiment, the substrate includes a reflective surface. The substrate may comprise, but is not limited to, one of the following materials: glass, metal, ceramic, or plastic.

The viewing window may be a cover slip made from, but not limited to, glass, borosilicate glass, glass that is toughened or stiffened, sapphire, plastic, vinyl, PVC, quartz, polymers, Thermanox™ (polymer in the polyolefin family), silicon nitride, or graphene.

A needle may be used to supply the gas bubble between the viewing window and biofilm.

The biofilm is developed on a substrate immersed in an aqueous medium.

In one embodiment, the apparatus further includes a white light interferometer to generate and capture interference fringes of the biofilm. Software may be used to control operation of the white light interferometer.

In one embodiment, the space between the substrate and the viewing window is enclosed in a casing that has an inlet and an outlet, forming a flow cell. The window region enables growth and monitoring of the biofilm. The flow cell is suitable for automated monitoring of growth of the biofilm in dynamic conditions.

In one embodiment, the flow cell is coupled to one or more pumps that provide a supply of liquid media and one or more gas bubbles to the biofilm. The one or more pumps include a first pump for providing the liquid media to a region between the substrate and the window, and a second pump for introducing the gas bubble to the biofilm.

In one embodiment, the apparatus comprising the flow cell includes a plurality of individual flow cells.

The apparatus can monitor changes in the topology and thickness of the biofilm in response to changes in the local environment. The local environment is the structure, composition, and chemistry of materials of the viewing window and the substrate.

The apparatus can also be used for biomedical and environmental screening and/or to measure effects of chemicals or drugs on the biofilm. Other applications are contemplated as discussed herein.

In another embodiment of the present invention, an apparatus for measuring biofilm surface properties is disclosed. The apparatus comprises a flow cell. The flow includes an inlet, and outlet, a window, and a substrate. The apparatus also includes a biofilm including one or more microorganisms grown on the substrate of the flow cell. The apparatus further includes a gas bubble introduced between the window and a surface of the biofilm.

In another embodiment of the present invention, a method of measuring biofilm surface properties is disclosed. The method includes growing one or more microorganisms on a substrate to form a biofilm. The method further includes placing a viewing window over the biofilm. The method also includes introducing a gas bubble between the viewing window and the surface of the biofilm.

In another embodiment of the present invention, an apparatus for measuring biofilm surface properties is disclosed. The apparatus includes a multi-well plate containing a plurality of individual wells. Each well has a base. The apparatus also includes a biofilm including one or more microorganisms grown on the base of the wells. The apparatus further includes a gas bubble localized on a surface of the biofilm.

In one embodiment, the multi-well plate contains, but is not limited to, 1, 2, 6, 12, 24, 48, 96, 384, or 1536 individual wells.

In one embodiment, the base of the well is a flat, transparent material.

In one embodiment, the plurality of individual wells is in an inverted configuration or orientation. In this embodiment, each of the plurality of inverted wells is oriented or configured with its base at the uppermost end of the plate.

In one embodiment, the microscope system includes a stage to allow the multi-well plate to be inverted automatically.

In another embodiment of the present invention, a method of measuring biofilm surface properties is disclosed. The method includes growing a biofilm including one or more microorganisms on a base of one or more wells of a multi-well plate containing a plurality of individual wells, with each well having a base. The method also includes localizing a gas bubble on a surface of the biofilm. The method further includes capturing data of the biofilm using a microscope system.

In one embodiment, the plurality of individual wells is inverted. Each of the plurality of inverted wells may be oriented with its base at the uppermost end of the plate.

The method further comprises a microscope system that can include a stage to allow the multi-well plate to be inverted automatically.

BRIEF DESCRIPTION OF THE DRAWINGS

FIG. 14A is a schematic diagram of a biofilm cultured in a well of a multi-well plate in an upright orientation.

FIG. 14B is a schematic diagram of a biofilm cultured in a well of a multi-well plate in an inverted orientated and coupled to the objective lens of a WLI, in accordance with one embodiment of the present invention.

FIGS. 16A-16F show exemplary images captured from biofilms grown in a 96-well plate. FIG. 16A shows a microscope slide prior to inoculation with bacteria.

FIG. 16B shows the slide with nutrient broth but no bacteria. FIGS. 16C-16F show growth of *pseudomonas fluorescens* biofilm at increasing times after inoculation: FIG. 16C: 7 days, FIG. 16D: 8 days, FIG. 16E: 9 days, and FIG. 16F: 10 days.

FIG. 19 is a 3D image of a *Pseudomonas fluorescens* biofilm grown in a flow cell.

FIGS. 20A-20C show images of a biofilm of *Pseudomonas fluorescens*. FIG. 20A shows the biofilm grown for 7 days. FIG. 20B shows the same location in the viewing window after 30 minutes exposure to bleach. FIG. 20C shows the same location after 1 hour exposure to bleach.

FIG. 21A is single frame of data captured during a WLI measurement of the biofilm. FIG. 21B shows a 3D profile image. FIG. 21C is a line profile from the white line in FIG. 21B.

DETAILED DESCRIPTION OF THE PREFERRED EMBODIMENTS

Figure 1:
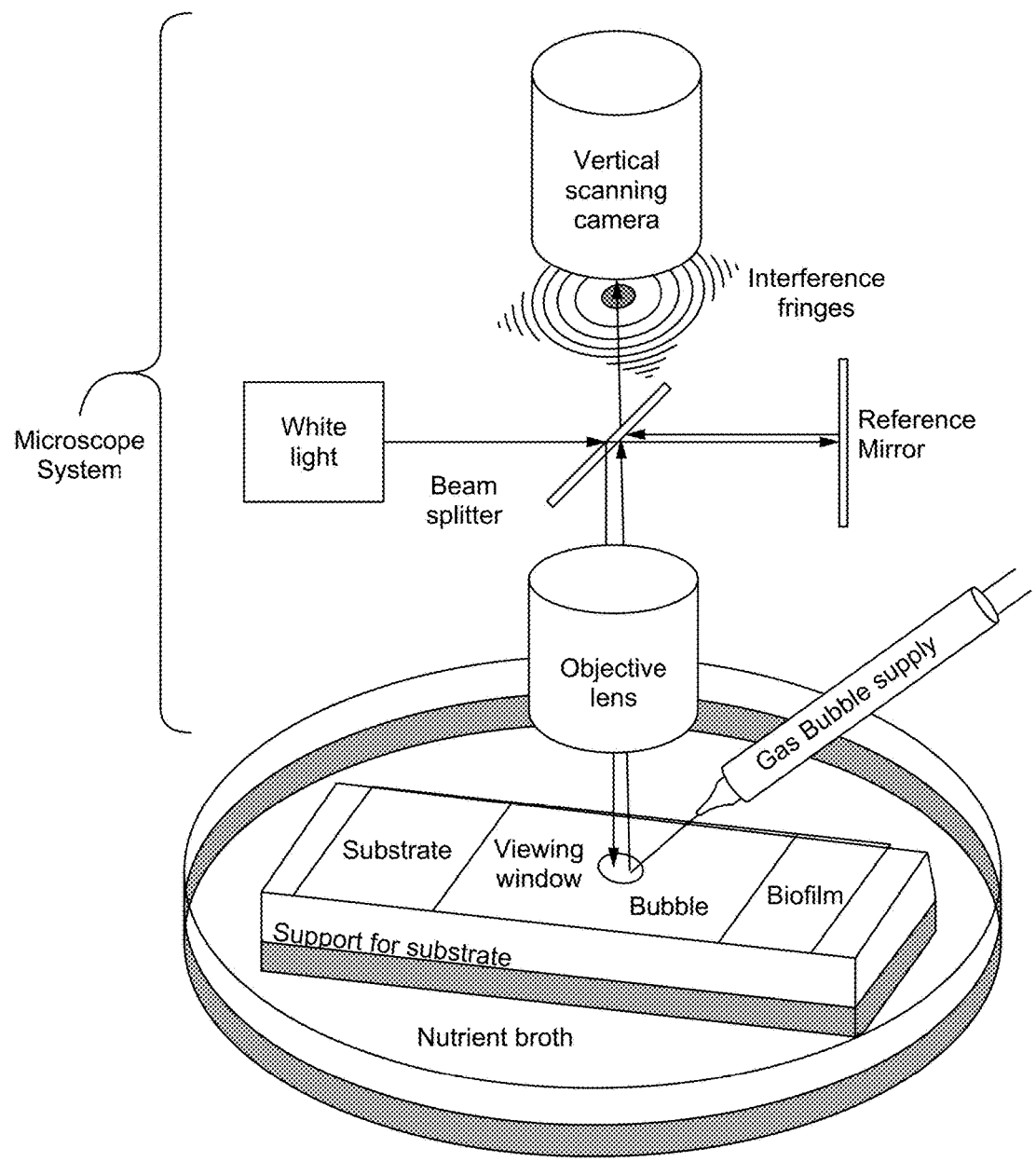
FIG. 1 is a schematic diagram of an apparatus for measuring biofilm surface properties, in accordance with one embodiment of the present invention.

The following description includes embodiments of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Disclosed are methods and apparatuses for measuring biofilm surface properties. In one embodiment, the measurement of thickness, volume and topology, including surface roughness and surface morphology, of live biofilms using a microscope system is disclosed.

The present invention also describes applications that demonstrate its unique abilities and advantages over existing biofilm imaging systems. These applications include, but are not limited to, the following: measuring texture and thickness of biofilms; monitoring growth of microbial communities, such as response to changes in the environment; tracking cells as they attach to surfaces, form colonies, and grow into mature biofilms; biomedical and environmental screening; observing and monitoring changes in biofilm structure in response to structure, composition, and chemistry of materials; and measurement of effects of chemicals or drugs on biofilms.

This invention describes methods and apparatuses for biofilm imaging in static conditions. This invention also describes methods and apparatuses for biofilm imaging in dynamic conditions using a flow cell. This invention further describes methods and apparatuses for biofilm imaging in the controlled environment of a multi-well plate. Each of these embodiments of the present invention offer unique capabilities that cannot be matched by existing biofilm imaging systems.

A biofilm is a community of microbes. It can be composed of a single species or multiple species of bacteria, single-celled, and multi-cellular organisms. Biofilms can have eukaryotes and prokaryotes. The biofilm may contain no organisms but may contain substances produced by living organisms. A biofilm may be taken to represent any cellular growth on a surface. A biofilm may be any thin film of biological origin attached to a surface. The organisms contained in the biofilm may be living at the time of the measurement and may be immersed in liquid. It will be clear that this invention can apply to any biological sample that one may choose to study. No limitation is intended.

In one embodiment the microscope system is a 3D profiling microscope that employs white light interferometry (WLI). This invention describes unique apparatuses and methods that enable WLI systems to image live biofilms. The surface morphology, surface roughness and biofilm thickness can be measured non-destructively and with high resolution over time without apparent disruption of the biofilm activity and processes. Also disclosed are applications for WLI biofilm imaging.

In one embodiment, the microscope system may be an optical profiling microscope. The microscope system may use focus variation, confocal scanning, structured illumination, or white light interferometry to capture a 3D profile. White light interferometry, white light interferometer, white light interferometric microscope, optical profiler, and optical profiling microscope may all refer to microscope systems that may be used in embodiments of this invention.

The present invention offers the ability to obtain high resolution 3-D profiles of biofilms as they grow. White light interferometry can produce 3-D maps of large areas (e.g., 2×3 mm) of the biofilm surface with extremely fine vertical resolution (e.g., <3 nm). This unique combination of fine vertical resolution with wide field of view enables accurate measurement of biofilm surface roughness. It was shown that a surface being overtaken by a bacterial biofilm roughens before there is any noticeable change in thickness.

Further, this invention offers an apparatus and method of in situ, dynamic observation and monitoring of biofilms. These embodiments include an engineered flow cell apparatus that is specific to the unique mode of WLI imaging described herein and a multi-well plate used in a non-standard inverted configuration.

Data collection methods, herein disclosed, capture information about the biofilm from multiple interference fringes that appear sequentially in a vertical scan.

The biofilm samples remain wet during measurement, which minimizes disruption. The invention allows multiple non-destructive measurements to be made on the same sample over time.

The surface profile of the biofilm can be observed even when the refractive index difference between the biofilm and the surrounding liquid is insufficient to induce interferometric fringes. This is accomplished by confining growth of the biofilm to a region between two parallel surfaces—a substrate and a viewing window—and then introducing an air/water interface in a small localized area at the surface of the biofilm. In some embodiments the substrate may be reflective but it is not necessary to be reflective for all embodiments. In some embodiments the viewing window is smooth, reflective, and transparent. In some embodiments the viewing window is a cover slip. Cover slips are thin flat pieces of transparent material that are placed over objects for viewing in a microscope. The cover slip may be made from glass, borosilicate glass, glass that is toughened or stiffened, sapphire, plastic, vinyl, PVC, quartz, polymers, Thermanox™ (polymer in the polyolefin family), silicon nitride, or graphene. This list is not intended to be limiting.

In some embodiments the viewing window does not shift the imaging focal plane. In some embodiments this will require that the viewing window is thin. In some embodiments, the viewing window is smooth, rigid, and transparent. These factors may limit the thickness of the viewing window. The viewing window may have a thickness between 100 and 300 microns or, in other embodiments, a thickness between 1 and 300 microns. The viewing window may be a two-dimensional material such as graphene and have negligible thickness. No limitation is intended on the thickness of the viewing window.

In some embodiments, the space between the substrate and the viewing window may be 50 and 500 microns in some embodiments. In other embodiments, the space between the substrate and the viewing window may be between 10 microns and 5 millimeters. No limitation is intended.

A simple gas or air bubble creates this reflective surface on the biofilm and enables WLI measurement. The gas may be nitrogen, oxygen, carbon dioxide, air, argon, and other gases. No limitation is intended. The gas can be carefully introduced with, but not limited to, a micro-controlled syringe pump. The pump may be connected to a needle, probe, or filament. Because the air is localized, the biofilm can remain fully hydrated, minimizing disruption of natural processes. The biofilm can continue growing and be measured repeatedly.

In some embodiments, the substrate and window are enclosed with an inlet and an outlet, forming a flow cell apparatus. The enclosure or casing may be made from glass, metal, polymer, ceramic, or plastic. No limitation is intended on the composition of the casing. In some embodiments, the flow cell will have a septum or more than one septa, ports, or openings. These may be used to insert air, microorganisms, liquids and other materials into growth area of the biofilm or to remove a sample from the biofilm or liquid.

In some embodiments, the flow cell is connected to a pump that supplies liquid media to it. Liquid media may be any liquid that supports biofilm growth. Liquid media may be water, or mixtures of water with other substances. No limitations are intended on the type of liquids that may be used.

In some embodiments, a multi-well plate is used in a non-standard configuration to grow and image biofilm. The base of each well serves as a viewing window. Properties of the base/viewing window are the same as the embodiments described above. For growth and culturing of biofilm, the well-plate is used in an upright configuration. At the time of imaging, the well-plate is inverted such that the viewing window at the base of each well is at the top where it faces the objective lens of the microscope. Inverting the well-plate serves the purpose of allowing air that was previously in the headspace of each well to rise and until it is adjacent to the biofilm attached to the viewing window. In some embodiments, a lid or sealing film may be used to contain liquid in the plate when inverted. In some embodiments, the microscope system may have a stage that allows the multi-well plate to be inverted automatically.

In some embodiments, the apparatus and method will be used to monitor changes in topology and thickness of a biofilm in response to changes in a local environment, or the structure, composition, and chemistry of materials of the viewing window and the substrate. In some embodiments, the present invention will be used for biomedical and environmental screening. Biomedical screening may be used to test the effects of drugs or chemicals on biofilms and their structure and topology. Embodiments of this invention will be used for many applications in biology and life sciences.

The present invention does not require a separate water filled perfusion cell or biomolecular staining as in other high resolution live cell microscopy techniques, so it can be used with any living or non-living biological material, including mixed communities of microorganisms. The preset invention takes advantage of the fine vertical resolution of WLI microscopes to measure surface features of biofilms over large areas. It does so very quickly and without contacting or disrupting the biofilm. In fact, it allows the biofilm to continue to grow uninhibited. Time series measurements that were previously impossible are now possible as a result of this invention. Further details of various embodiments of the present invention will be explained further in the examples below.

EXAMPLES

Introductory Material for Examples

The following examples from a study serve to illustrate embodiments and aspects of the present invention and are not meant to be construed as limiting the scope thereof.

This introductory section describes the microscopes, microscope parameters, microorganisms and biofilm culturing conditions that were used for all of the subsequent numbered examples. Interferometric optical microscopes were used to characterize the surface profile and thickness of biofilms. Two microscope systems were used for optical profiling. Profilometry was performed using a white light interferometer in vertical scanning interferometry (VSI) mode, in which the microscope head is translated vertically until the sample passes through the focal plane. A 2.5× interferometric objective lens was used to obtain a 2.5 by 1.9 mm field of view. The microscope contains an imaging sensor that can record 100 frames per second. A computer connected to the instrument recorded image frames as the objective lens scanned vertically. The software analyzes each pixel in the image and assigns vertical positions in order to construct a 3D profile image. The noise rejection threshold, which identifies the acceptance criteria for fringe packets, was set to its minimum value in order to capture any and all interference fringes created by the top of the biofilm.

For all examples presented below, the horizontal resolution of the 2.5× objective lens was 3.7 µm. The resolution is sufficient to resolve the features present in bacterial biofilms, which are generally on the order of the individual bacteria themselves—1-10 µm.

Biofilms of *Pseudomonas putida* (ATCC 39169) and *Pseudomonas fluorescens* (ATCC 13525) were grown on glass substrates. *P. putida* is a gram-negative bacterium found in soil and water. It has been studied extensively due to its diverse metabolism. *P. fluorescens* is a common gram-negative bacterium. For each experiment dense bacterial culture (~$10^8$ CFU/ml) was added to sterile nutrient tryptic soy broth (TSB) and the mixture was then placed on or passed over the substrate where bacteria settled and formed biofilm. WLI surface profiles were collected as the biofilm grew. The biofilms were left undisturbed on the stage of the microscope between measurements and were exposed to ambient temperature in the laboratory (~21° C.). Though the biofilms were covered or enclosed between data collection, no extraordinary measures were taken to prevent contamination from the environment as the purity of the microbial colony was not important for these examples.

Example 1

Apparatus for Interferometric Measurement of Biofilm

This example describes an apparatus that enables WLI imaging of biofilms. The apparatus serves a platform for biofilm growth and has properties that enable WLI imaging. FIG. 1 is a schematic diagram of an apparatus for measuring biofilm surface properties, in accordance with one embodiment of the present invention. FIG. 1 shows the microscope system, a substrate for growing biofilm, a viewing window, and a gas bubble. The microscope system consists of the objective lens, beam splitter, white light source, reference mirror, and vertical scanning camera. As seen in FIG. 1, white light is aimed at a beam splitter. Part of the beam is directed to the part of the biofilm sample that is covered by a gas bubble while the remainder is reflected off of a smooth reference mirror. The reflected light from these two surfaces is recombined on the camera, which contains an imaging detector, to create interference fringes when the optical path length of the experimental and reference beams are nearly equal. Data collected by the microscope system is used to construct a 3D profile of the surface of the sample.

The microscope stage was arranged to support a growth platform for biofilm, as shown in FIG. 1. Normally the platform or substrate, such as an ordinary microscope glass slide, positioned on a support was submerged in nutrient broth that promotes bacterial growth. The broth may be contained in a petri dish as shown in FIG. 1, though the petri dish is not a necessary component of this invention. Other embodiments use other means to provide a substrate in a liquid environment. For in situ non-destructive measurement the biofilm remains wetted. Then a viewing window (24×50 mm glass cover slip with 0.16 to 0.25 mm thickness) is placed over the surface of the biofilm. The cover slip and the microscope slide provide the reflective surfaces that enable interferometric assay of the wet biofilm.

A fine (31G) needle is inserted between the cover slip and the surface of the biofilm in order to introduce a small volume of air over the biofilms, as shown in FIG. 1. The bubble is adjacent to a small area of the biofilm surface. The resulting air/biofilm interface was highly reflective and revealed the underlying structure of the biofilm's surface without being destructive to the fragile structure. The introduction of the air/biofilm interface is a key aspect of this invention. Without it, WLI imaging of biofilms was not previously possible.

Air was supplied to the needle using a syringe pump. The needle was fixed to the underside of the viewing window (a glass cover slip in this case) and polyimide tape formed a ring around the tip of the needle to help contain a small volume of air. The total volume of air introduced was typically on the order of 1-5 µl resulting in an air headspace on the order of 150-250 µm, as measured from top to bottom.

Figure 21C:
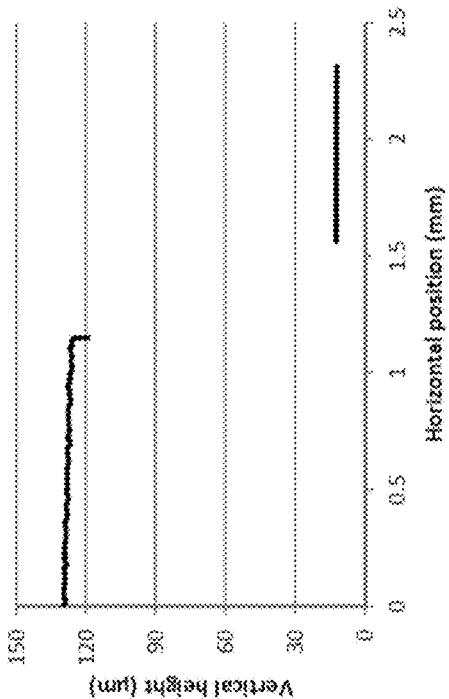
FIGS. 21A-21C illustrate the positioning of the air bubble in the field of view of the microscope.
Figure 21A:
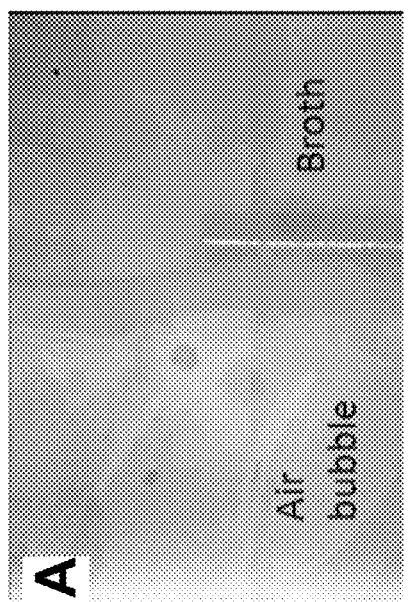
Figure 21B:
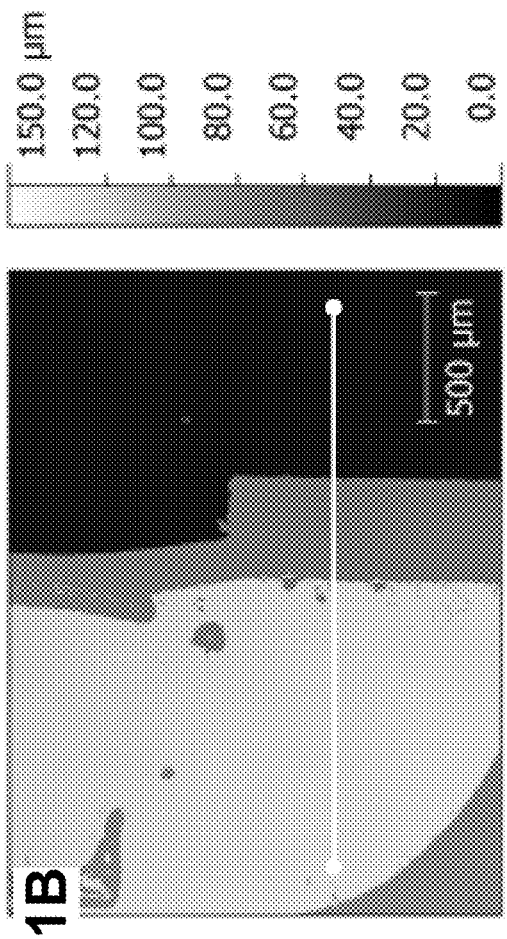

FIGS. 21A-21C illustrates the positioning of the air bubble in the field of view of the microscope. FIG. 21A is a single frame of data captured during a WLI measurement of biofilm. The left side of the image has an air bubble and the surface of the biofilm is seen. The right side of the image has liquid nutrient broth continuous from the cover slip to the substrate, so light cannot reflect from the surface of the biofilm. In the right side of the image, light passed through the biofilm and was reflected from the underlying substrate. The needle used to insert the air bubble is seen at the middle.

This apparatus enables WLI imaging of biofilms. Selected examples shown below demonstrate the unique capabilities of using this apparatus. The method for using this apparatus will be described in detail in Example 2.

Selected Examples of WLI Biofilm Images

Thickness of two biofilms of *Pseudomonas putida* was measured through time in order to observe growth. The first biofilm was grown for four days and the second was grown for six days. In addition, root mean squared roughness ($R_q$) was measured using open source profile analysis software. Roughness was measured from selected areas (0.5 by 1.0 mm) of the image that contained only the biofilm surface.

Figure 6A:
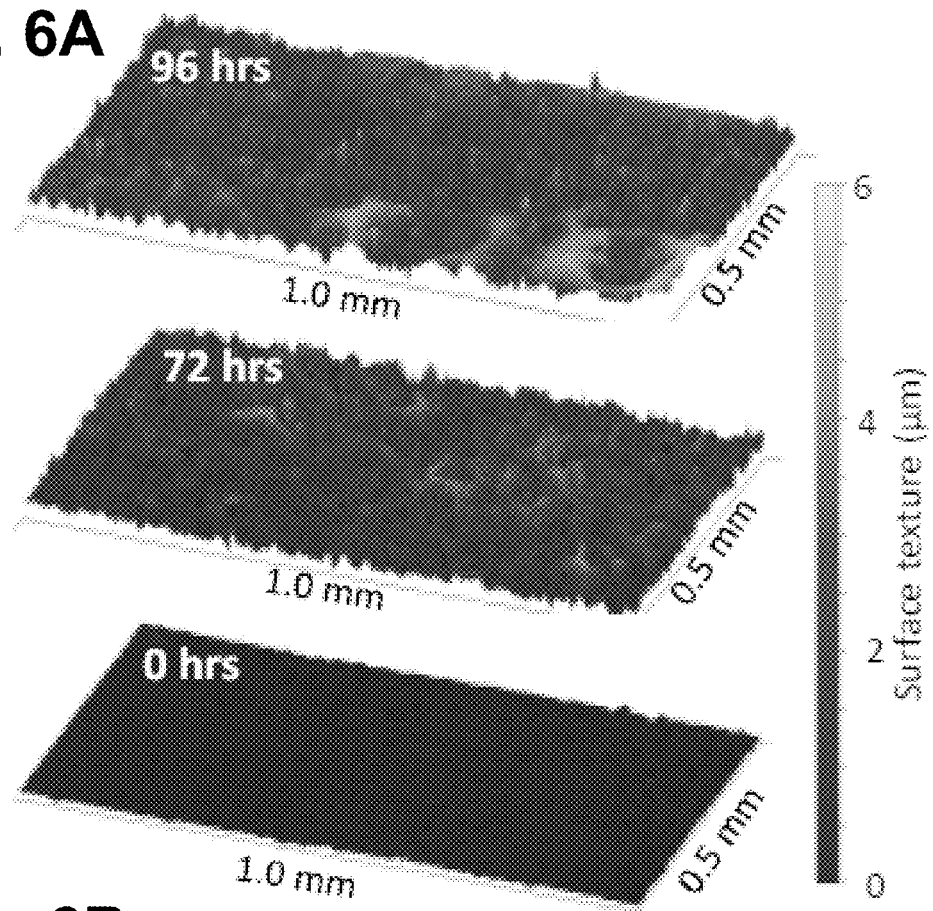
FIG. 6A shows selected surface profiles of the biofilm at 0, 72, and 96 hours, depicting a gradual increase in surface roughness of the biofilm over time.

FIG. 6A shows selected surface profiles of the biofilm as it grew over 96 hrs. The false color scale in FIG. 6A reflects amplitude of surface texture of the biofilm and not the full thickness. Note that each image came from the same general area on the sample but not necessarily from the same spot. Root mean squared roughness ($R_q$) was calculated from each profile. Roughness increased with time, as would be expected during the growth of a biofilm. At the beginning of the experiment, shortly after inoculating with a culture of bacteria (hours=0 in Figures), the surface of the microscope slide had little texture ($R_q$=0.16 µm). As time progressed and the biofilm grew the observed surface became rougher—rising to $R_q$=0.92 µm after 96 hours.

Figure 6B:
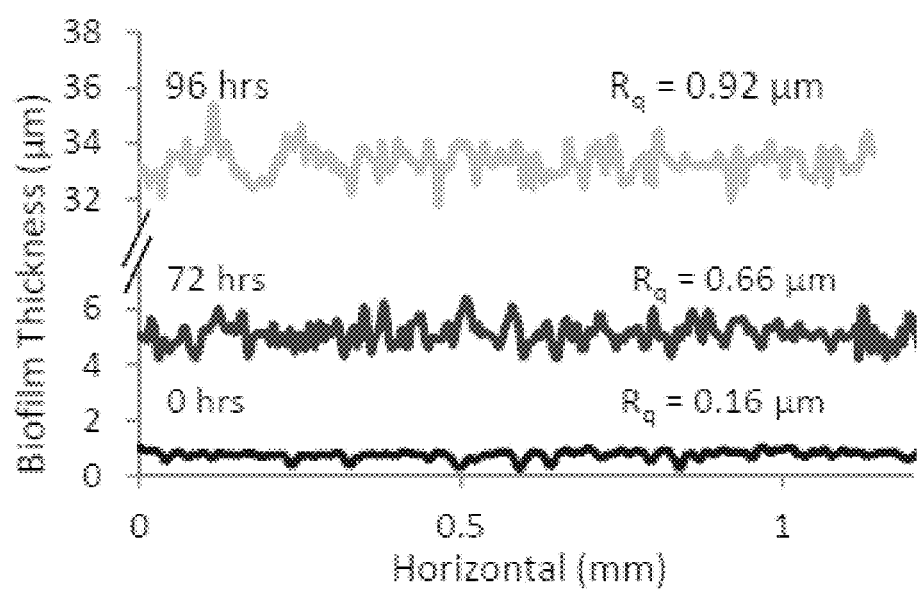
FIG. 6B shows linear profiles extracted from each of the profiles in FIG. 6A.

FIG. 6B shows linear profiles extracted from each of the profiles in FIG. 6A and placed on a vertical scale at the appropriate vertical positions as measured by the method described herein. Thickness increased with time—reaching 33.9 µm after 96 hours. This figure demonstrates the high resolution profile information that can be attained with WLI microscopy. Prior to this invention it was more difficult to distinctly observe the interface of a biofilm and such measurements were less accurate.

Figure 7A:
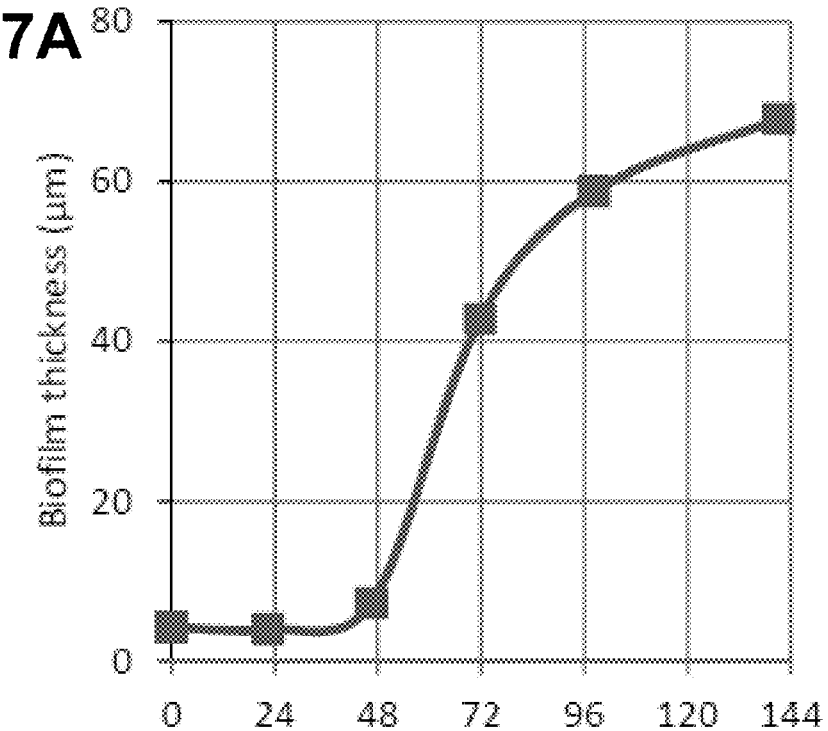
FIG. 7A shows thickness of P. putida biofilms grown and monitored for over 144 hours.
Figure 7B:
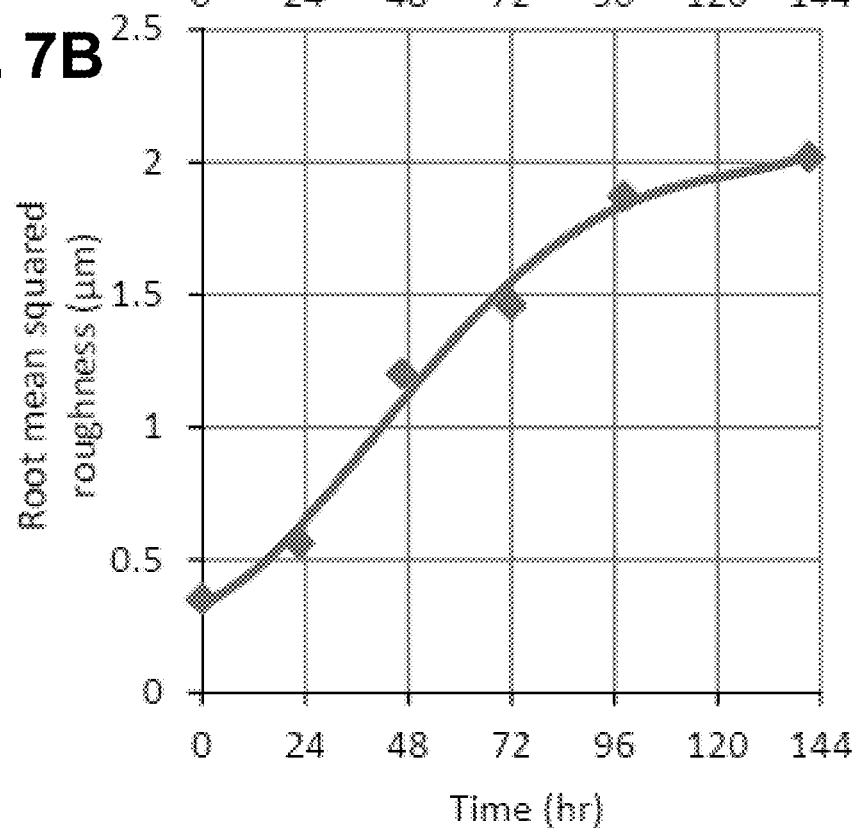
FIG. 7B shows the root mean squared roughness of the P. putida biofilms of FIG. 7A for the same amount of time.

A different biofilm sample was grown and monitored for approximately six days. The thickness and root mean squared (RMS) roughness of the biofilm over this time are shown in FIGS. 7A and 7B. FIG. 7A shows thickness of *P. putida* biofilms grown and monitored for over 144 hours. Thickness follows an expected growth curve with a lag phase, followed by exponential growth and finally by a stationary phase with maturity after four days. After staying below 10 microns in the first 48 hours, the biofilm then grew to more than 67 µm. FIG. 7B shows the RMS roughness of the *P. putida* biofilms of FIG. 7A for the same amount of time. RMS roughness also increased with time. Both this and the previous biofilm showed a slow rate of initial growth followed by a period of rapid growth and finally another period of slowed growth. Such growth curves are commonly seen for bacterial growth in closed-cell environments such as petri dishes or test tubes. This result demonstrates that WLI imaging can observe trends that are consistent with other methods.

It can be seen in FIGS. 7A and 7B that there was a noticeable increase in roughness in the first 24 hours whereas the thickness only increased significantly after 72 hours. This increase is likely the result from the formation of a conditioning film and initial colonization processes, which are typical precursors to mature biofilm formation. The data clearly indicates that roughness could be used as an early indicator of biofilm growth that is measurable before a biofilm of any appreciable thickness is formed. WLI microscopy of biofilms, as enabled by this invention, could be a particularly effective tool to investigate prevention strategies that target early stages of biofilm growth, including conditioning film and bacterial attachment.

Example 2

Method for Interferometric Measurement of Biofilm

This example describes the method for using a WLI microscope to measure thickness and surface profile of *P. putida* biofilms. First, biofilm was grown on a substrate according to the conditions described above. At the time of measurement a viewing window (a cover slip in this case) was gently lowered onto the surface of the biofilm. In water, the top surface of the biofilm does not have a reflective interface due to lack of refractive index contrast (the biofilm is mostly water resulting in nearly matching densities), so a bubble was introduced between the sample and the viewing window using a syringe needle. A pump was used to direct a small volume of air through the needle to the surface of the biofilm sample. The resulting air/biofilm interface was highly reflective and revealed the underlying structure of the biofilm's surface.

The microscope's positioning controls were used to lower the objective lens to a position where interference fringes were visible in the microscope image. Then a microscope scan was initiated. In some embodiments the scan range was chosen to capture fringes from multiple surfaces during a single scan. When the scan was completed the microscope's software constructed a 3D image of the biofilm's surface. This image was then analyzed using open source data analysis software.

In some embodiments the cover slip was gently lifted from the surface of the biofilm at the conclusion of each WLI measurement and fresh broth was replaced in the dish until the substrate and biofilm were submerged in 3-5 mm of liquid so the biofilm could continue to grow. In some embodiments the viewing window was fixed in a set position above the substrate and it is not removed at any time during single or time series measurements.

For time series measurements, the same biofilm was measured multiple times over the course of several hours, days, or weeks. The non-destructive measurement process enabled repeated high resolution imaging of the same biofilm sample.

Measurement of Biofilm Thickness

Figure 2:
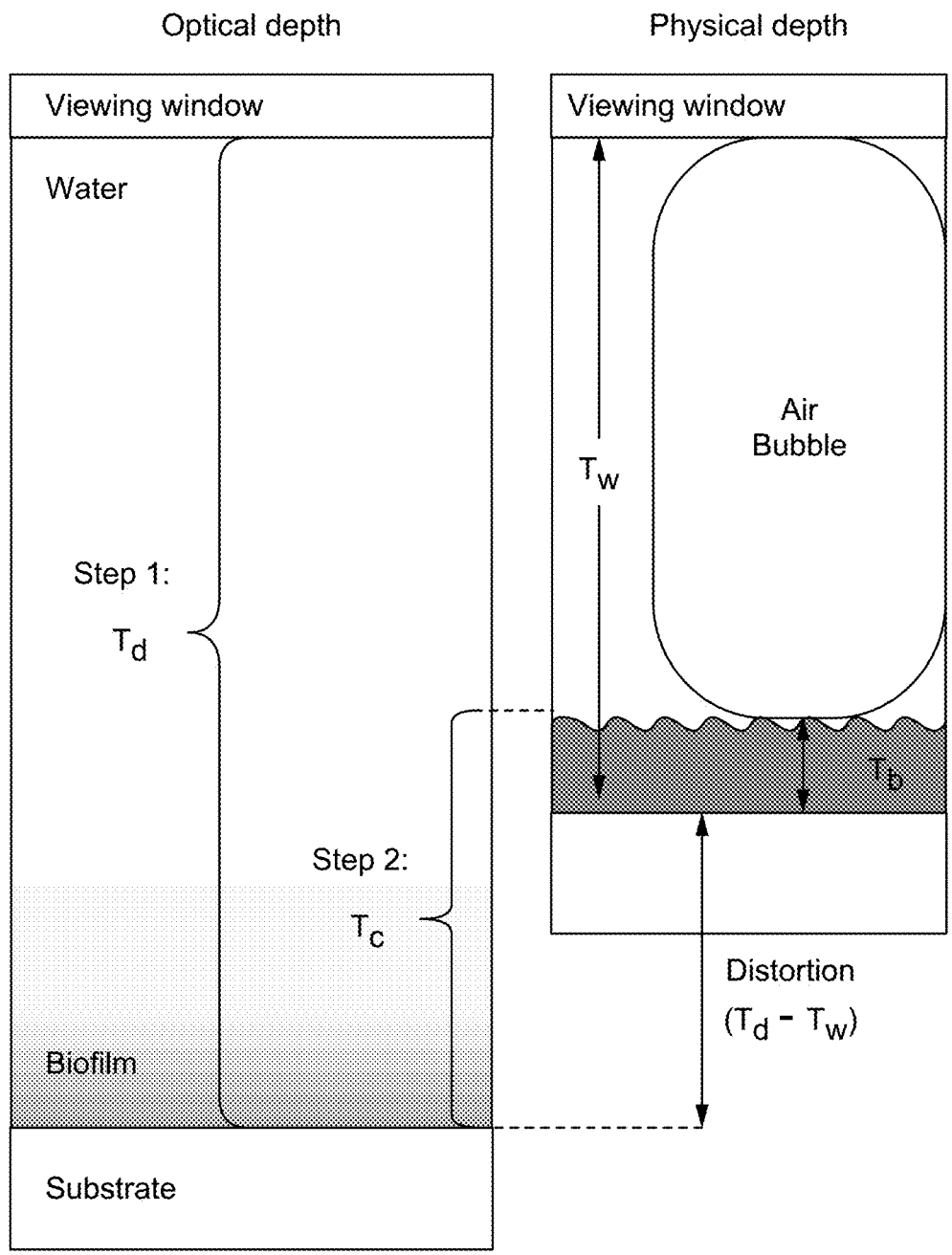
FIG. 2 is a conceptual schematic of a two-step process for measuring wet biofilm thickness with interferometric optical profiling.

After the viewing window was in place, as described above, two sequential WLI measurements were taken as illustrated in FIG. 2 which is a conceptual schematic of a two-step process for measuring wet biofilm thickness with interferometric optical profiling. Both steps are necessary in order to derive accurate biofilm dimensions. The first measurement (Step 1) is the optical depth of the layer of water between the cover slip and slide ($T_d$). The optical path length between the cover slip and the slide ($T_d$) was measured through liquid. The objective lens was lowered manually to the appropriate working distance and the sample was levelled using stage tilt controls. A vertical scan (~500 µm) was then initiated in the software that controls the operation of the microscope.

This first measurement captured the interference fringes caused by reflection from the lower surface of the cover slip and the upper surface of the underlying glass slide. Video of the scan was recorded to measure time between fringes. The optical path length was measured by multiplying the time interval between the appearances of the two fringe packets by the fixed scan rate (1.205 µm/s). Note that during this scan the hydrated biofilm's refractive index was so similar to that of water that no measurable Fresnel reflection was created by the film/water interface. The optical path length calculated ($T_d$) ends up being larger than the physical distance due to the effect of the high refractive index of water. Calculations to correct this distortion are described in detail below.

The second measurement (Step 2) is the optical distance from the surface of the biofilm in air to the surface of the substrate in water ($T_c$). This measurement spans physical and optical depth due to the presence of an air bubble. Distortion of optical depth is caused by higher index of refraction of water and is easily corrected with a calculation to give the physical depth of water ($T_w$). Subtracting distortion from $T_c$ gives the physical biofilm thickness ($T_b$). Measurements made by WLI are shown with brackets while calculated distances are shown with arrows. Measurement and calculation steps are shown in order from left to right.

A field of view that contains portions of biofilm with both air and water headspace was selected. Selection of such an area is made possible by carefully inserting the air bubble so it filled part of the microscope's field of view. Then a vertical scanning range was selected that was large enough to include both the surface of the biofilm and the microscope slide, the latter of which appears artificially lower due to the refraction of water. Where a small step from the surface to the base of the biofilm was expected, a significantly larger step was observed. This scan allows us to measure a distorted biofilm thickness, $T_c$, as shown in FIG. 2.

FIGS. 21A-21C demonstrate the selection of an appropriate field of view and the resulting profile image. FIG. 21A shows a field of view where the left side of the image is biofilm with a bubble over it and the right side of the image shows biofilm with liquid continuous from the viewing window to the substrate. FIG. 21B shows a 3D profile image that results when an appropriate vertical range is selected to capture these two surfaces, but not any interference fringes that might be seen from the lower surface of the cover slip. The color scale shown to the right of the image corresponds to vertical positions such that darker parts of the image are lower and lighter parts of the image are higher. The surface of the biofilm at left is elevated relative to the substrate at right.

FIG. 21C is a line profile from the white line in FIG. 21B. The line profile shows a step from left to right, which is the distorted biofilm thickness, $T_c$. This step height is not the true thickness of the biofilm because the position of the substrate in the right half of the image is lowered by the extended optical path length of light passing through water. However, the step height can be used to calculate the true thickness of the biofilm. FIGS. 21A-C illustrate that in some embodiments of this invention it will be desirable and necessary to position the air bubble within a field of view of the microscope such that there is at least one section of the field of view that is not filled by the biofilm.

In many embodiments of this invention it will be necessary to account for the optical distortion in the measurement of biofilm thickness by accounting for differences in refractive index between air ($\eta=1.0$) and water ($\eta=1.33$). In this example that distortion is evident in the distorted step height between two areas of the field of view. The physical thickness of the water+biofilm zone ($T_w$) was calculated from the distorted thickness ($T_d$). The correction is shown in Equation 1:

$$T_w = \frac{T_d}{\eta_i} \cdot \cos\theta_2 \qquad (1)$$

Where $\eta_i$ is the index of refraction of the medium (water) and $\theta_2$ is the angle of incidence of the light. Normally, the angle of incidence is just correlated to the numerical aperture of the lens; however, in this case, light passes through the cover slip and water. Since the edges of the cover slip are parallel to one another it can be ignored as a refracting medium: light refracted at the leading edge is effectively "un-refracted" at the lower edge. Applying Snell's law at an air-water interface with angle of incidence ($\theta_1$), given by the numerical aperture of the objective lens, gives $\theta_2$. The numerical aperture of the 2.5× objective lens used for this example is 0.075, which corresponds to $\theta_1$ of 4.3 degrees. The index of refraction of water (1.333) is not significantly impacted by the presence of biofilm. After $T_w$ is calculated using Equation 1, the distortion caused by water was calculated by simply taking the difference between optical and physical depths ($T_d$-$T_w$).

Interestingly, the distortion caused by water in the measurement of biofilm thickness is the same magnitude as in the first measurement from the cover slip to the slide through water. It is evident from FIG. 2 that the physical depth of the biofilm ($T_b$) is simply:

$$T_b = T_c - (T_d - T_w). \quad (2)$$

Equation 2 can then be applied to calculate biofilm thickness for each measurement in a time series and changes in biofilm thickness can be monitored. Thus, WLI measurements resulted in both a high resolution image of the biofilm surface and accurate measurement of biofilm thickness. This was accomplished without removal of any portion of the biofilm. The measurement process was validated with controlled non-living thin films, which will be described in the subsequent section.

Verification of Thickness Calculations

Since biofilm thickness values are based on calculations from equations 1 and 2, it was important to verify that these calculations result in accurate measurements. Films with known thicknesses were selected to serve as standards to confirm this measurement and calculation method. First, a layer of 2 mil polyimide tape was placed on a microscope slide. This tape is smooth, transparent, has consistent thickness, and reflects light from its surface analogous to what occurs at the surface of a biofilm during WLI image. The tape also has the advantage that its refractive index is significantly different from that of water so its surface can be observed even when submerged. The manufacturer-reported thickness of the tape, including the adhesive layer, is 3.5 mils or 88.9 μm. A drop of water was placed on the tape and then a cover slip was lowered onto the surface. Rather than introduce a bubble with a needle, a small bubble that was already present under the slide was manipulated to the edge of the tape. Then the thickness of the tape was measured using the method described above. With this control, a clear edge was present so the calculated thickness could be compared to both the manufacturer's specified thickness and the thickness measured "dry"—i.e., without a layer of liquid over the tape or the substrate.

Figure 3:
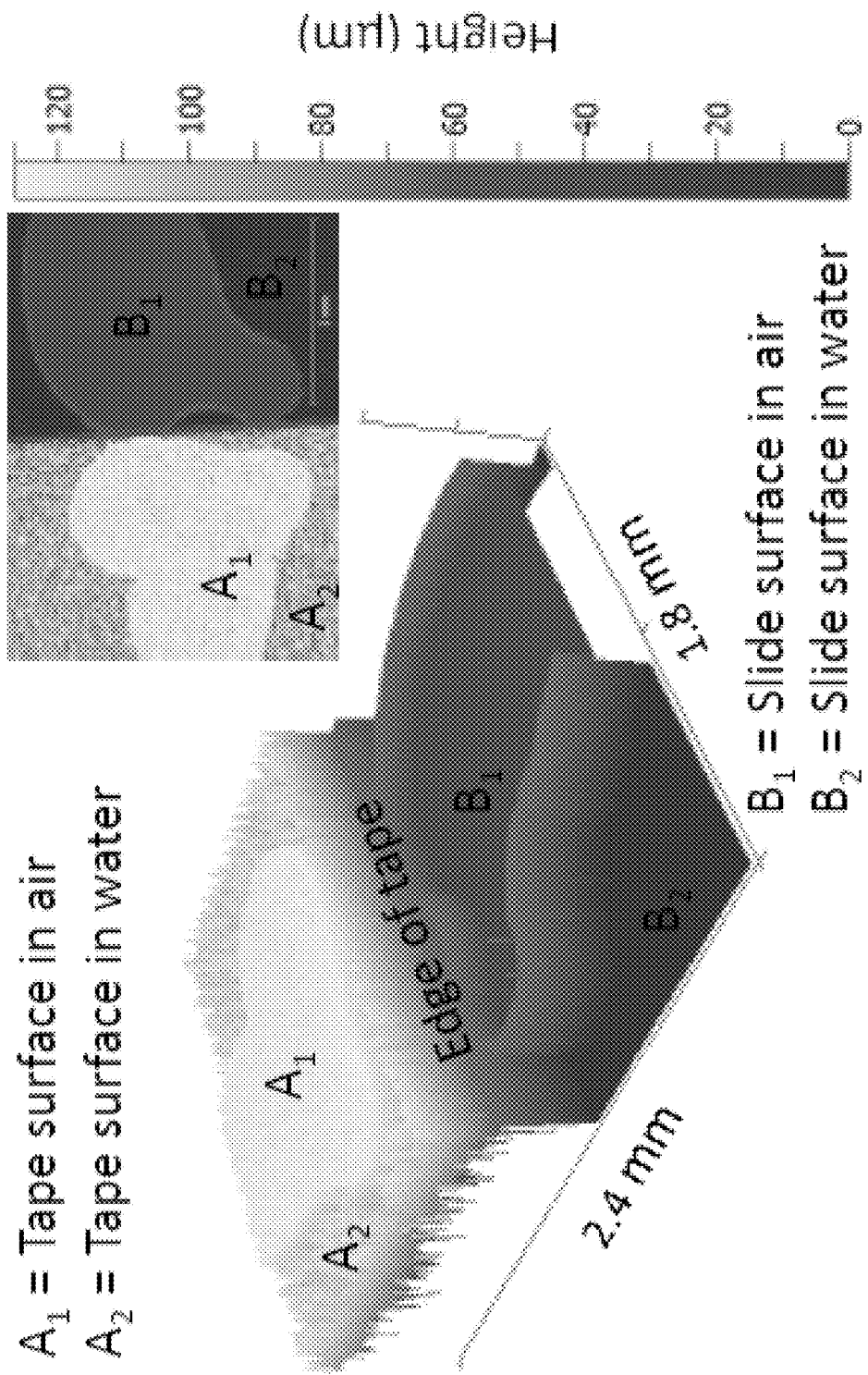
FIG. 3 is an optical profile of polyimide tape of known thickness that was imaged through a water layer and through a small air bubble that straddles its edge.

The surface profile from the WLI measurement "Step 2" is shown in FIG. 3, and data and calculations from this image are shown in Table 1 below. Four distinct surfaces are visible in FIG. 3. Areas $A_1$ and $B_1$ are the polyimide tape and substrate slide, respectively, imaged through air. Areas $A_2$ and $B_2$ are tape and slide, respectively, imaged through water; they appear lower than the same surfaces measured through air due to the longer optical path length through water. The vertical positions measured through water appear lower due to the longer optical length.

The surface labeled $A_2$ in FIG. 3 appears highly textured, though this is likely a convolution of the interference fringes from the top and bottom of the solid layer of the tape excluding the adhesive. This problem did not occur for $A_1$ because the fringes from that surface were much stronger in intensity and superseded fringes from lower surfaces.

TABLE 1

Example thickness calculation from measurements in FIG. 3

| | Thickness (μm) | |
|---|---|---|
| | Measured | Calculated |
| Step 1: Optical depth of water ($T_d$) | 145.2 | N/A |
| Step 2: Distorted tape thickness ($T_c$) | 122.5 ($A_1$ − $B_2$) | N/A |
| Calc. 1: Physical depth of water ($T_w$) | N/A | 109.0 |
| Calc. 2: Water distortion ($T_d$ − $T_w$) | 36.0 ($B_1$ − $B_2$) | 36.2 |
| Calc. 3: Physical film thickness ($T_b$) | 86.0 ($A_1$ − $B_1$) | 86.3 |

Note:
Tape manufacturer specifies thickness of 88.9 μm

From the first WLI scan, the optical thickness ($T_d$) of the water layer from the microscope slide to the cover slip (not shown) was calculated to be 145.2 μm. Next, the distorted film thickness ($T_c$) of the tape was measured. In the image of FIG. 3, it is the distance from $A_1$ to $B_2$, which is 122.5 μm.

The physical thickness ($T_w$) of the water between the cover slip and slide was calculated using Eq. 1 to be 109.0 μm. Distortion was calculated as the difference between optical and physical depths—36.2 μm. In the FIG. 3 image, the distortion was also measured directly using data from the section of the slide that was not covered in tape—it is simply the difference between $B_1$ and $B_2$ and was found to be 36.0 μm, which is in remarkable agreement with the value calculated from Eq. 1.

Completing the WLI thickness measurement assay using Eq. 2 to subtract distortion from $T_c$ resulted in a calculated tape thickness of 86.3 μm. Again, because the tape has a sharply defined edge its thickness was easily measured directly using WLI—it was simply the vertical distance from $A_1$ to $B_1$, which is 86.0 μm. This result was in excellent agreement (0.3% difference) with the measured thickness. Both measurements were slightly lower than the manufacturer's specified thickness of approximately 88.9 μm, which is likely an overestimate as it does not account for compression of the adhesive during application. Independent WLI measurements of this 2.5 mil polyimide tape in air showed that the actual thickness varied between 83 and 87 μm depending on specimen and location.

This result validates the calculation method described above. Tape thickness that was measured when submerged in water matched the thickness when measured dry. Measurements made from the image confirmed that shifts in optical path length occur due to refractive index of water and that the true physical distances can be calculated.

A second validation of thickness measurement was carried out with polystyrene (PS) spheres of known diameters. Spheres with 1, 2, 5.1, and 10.2 μm diameters were suspended in water and deposited on a microscope slide by placing a drop on the slide. The spheres formed rafts of monolayer films over the surface of the slide. The height of these particles was then measured using the method described above. Results were compared to the specified diameter of the manufacturer and to measurements made with WLI when the particles had completely dried.

Figure 4A:
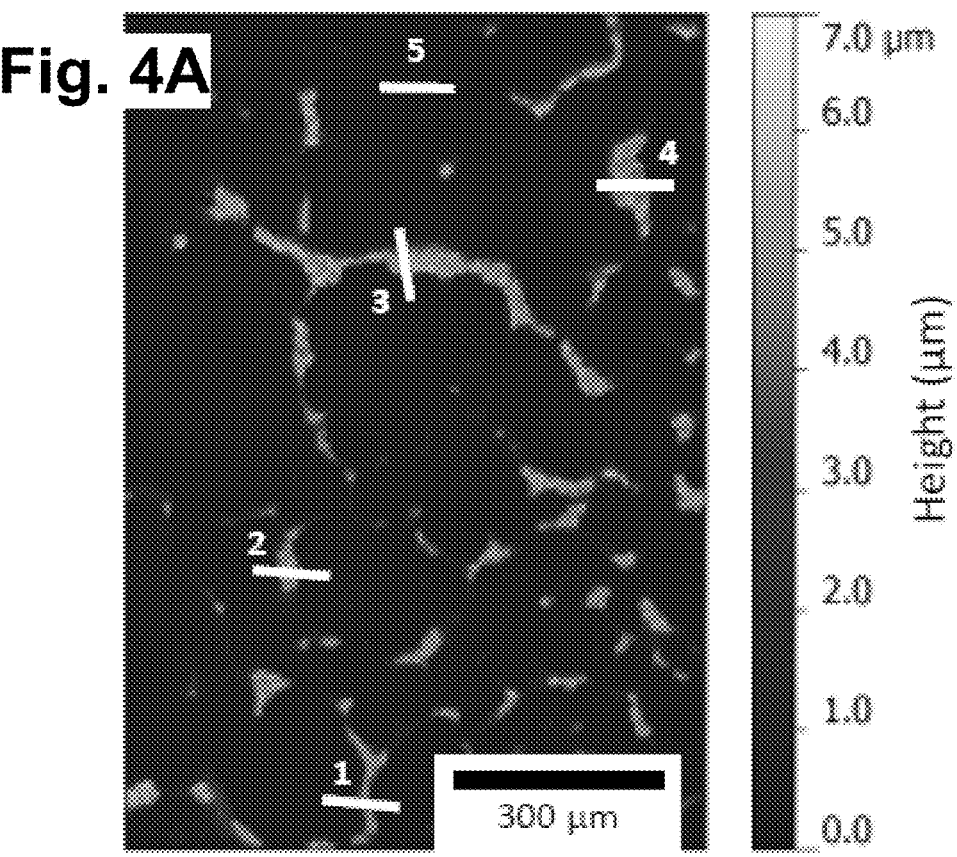
FIG. 4A is an optical profile of 5.1 μm polystyrene spheres on a glass cover slip.
Figure 4B:
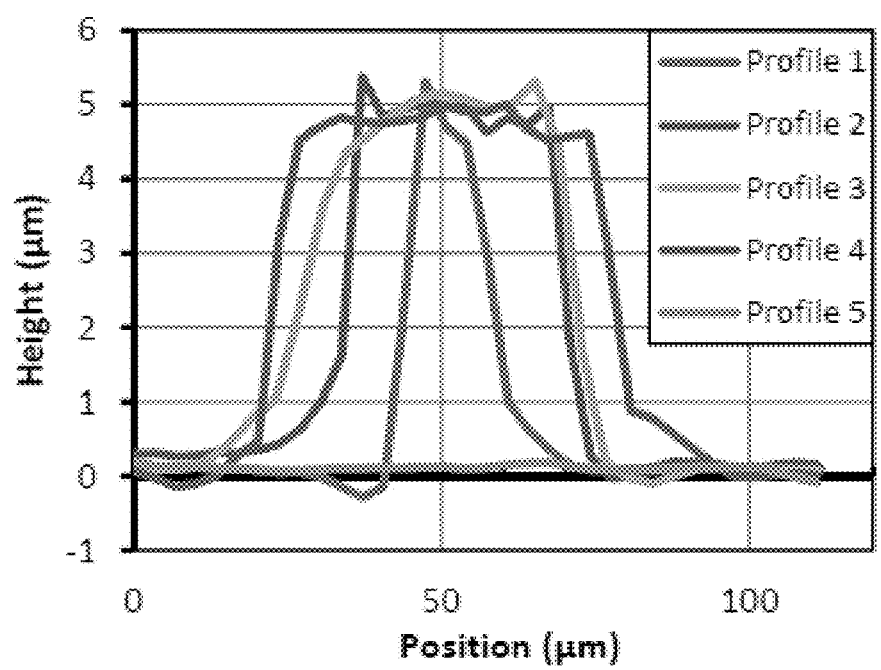
FIG. 4B are profiles from the five white lines marked in FIG. 4A, and Profile 5 shows the baseline with no particles.

FIG. 4A shows agglomerated rafts of 5.1 μm spheres on a glass slide. The lightest light color in the background is the baseline of the slide and the darker dark color shapes are the groups of spheres. Four line profiles of agglomerate rafts of spheres are shown in FIG. 4B. The fifth line profile shows the flat surface of the microscope slide. The diameter of the particles—measured by correcting distortion through liquid—was found to be 5.32±0.17 μm. The average peak-to-base height of all the profiles in FIG. 4b is 5.25±0.08 μm.

The two diameter measurements are virtually identical and both are within the specified 10% tolerance of the manufacturer's specified 5.1 µm thickness. Similar images and profile data for 10.2, 2.2 and 1.1 µm particles are shown in FIGS. 8A-8B, 9A-9B, and 10A-10C.

Figure 5:
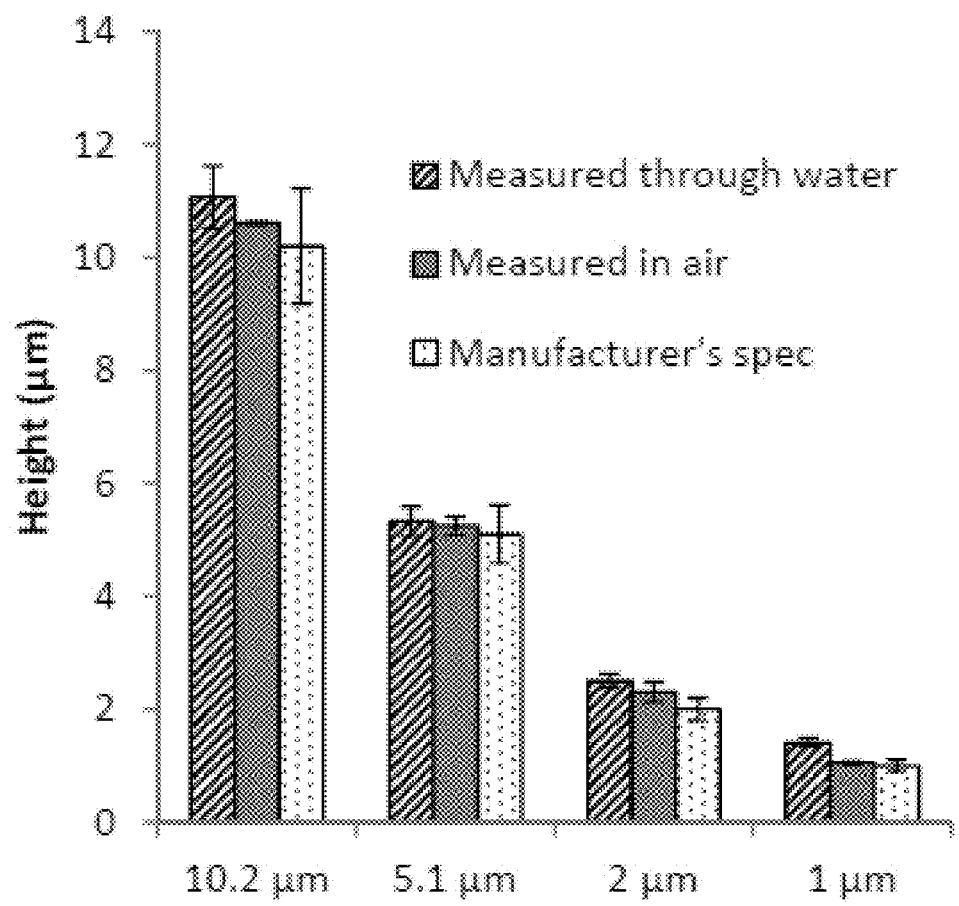
FIG. 5 is a graph to show comparison of the manufacture's specified diameter of the polystyrene spheres to heights interferometrically measured with and without distortion correction through water for all particles.
Figure 8A:
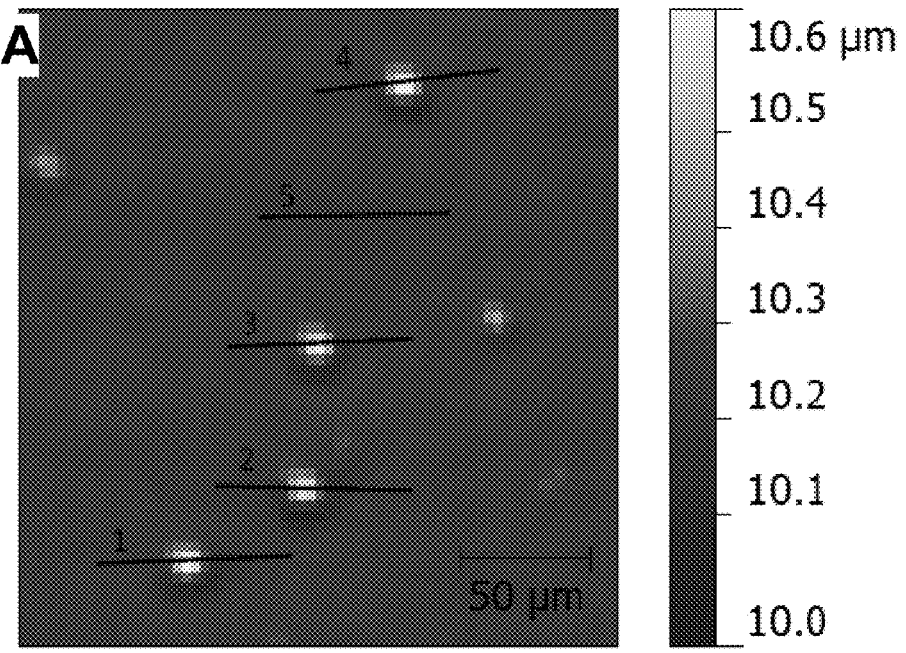
FIG. 8A is an optical profile of 10.2 μm polystyrene spheres on a glass cover slip.
Figure 8B:
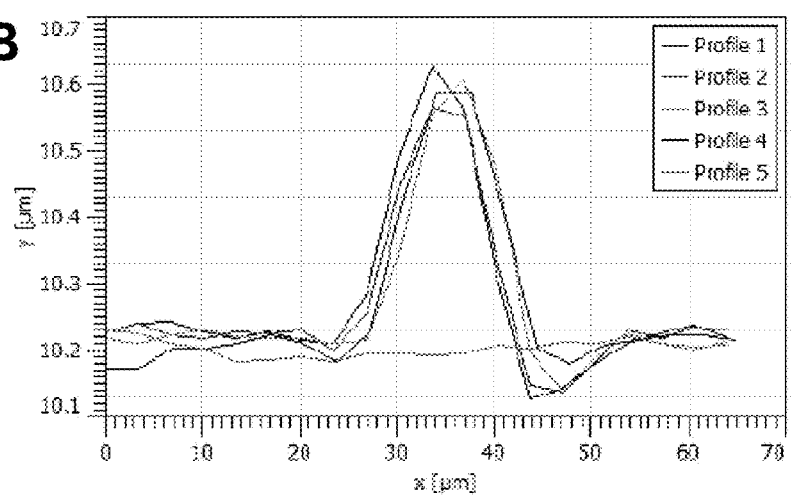
FIG. 8B shows vertical profiles from the lines marked in the image of FIG. 8A.
Figure 9A:
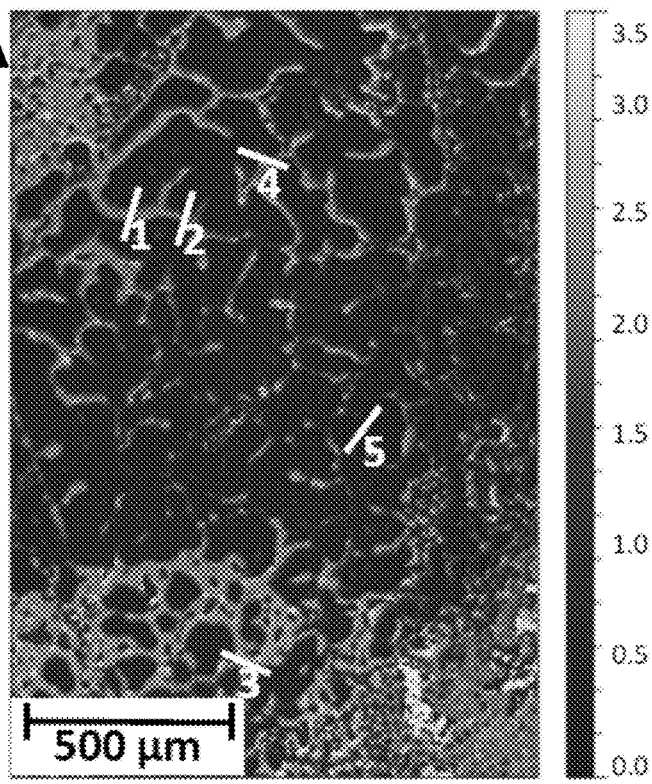
FIG. 9A is an optical profile of 2 μm spheres on a glass cover slip.
Figure 9B:
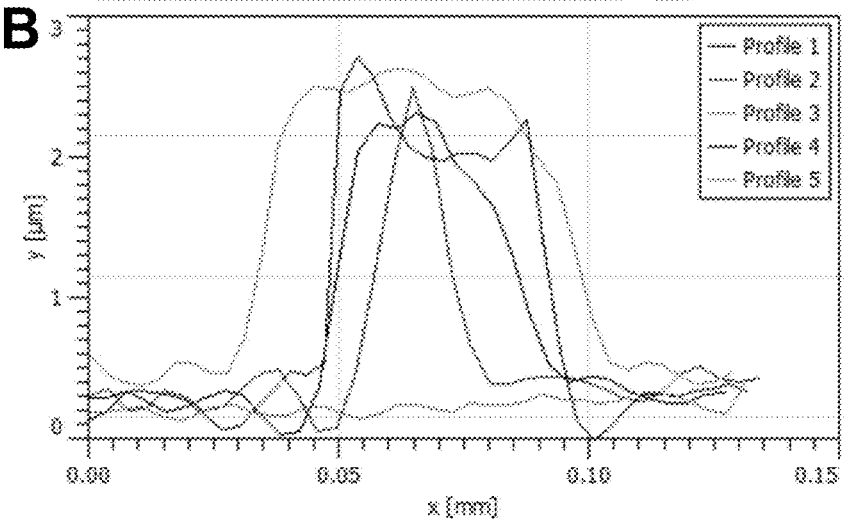
FIG. 9B shows vertical profiles from the lines marked in the image of FIG. 8A.
Figures 10A, 10B, 10C:
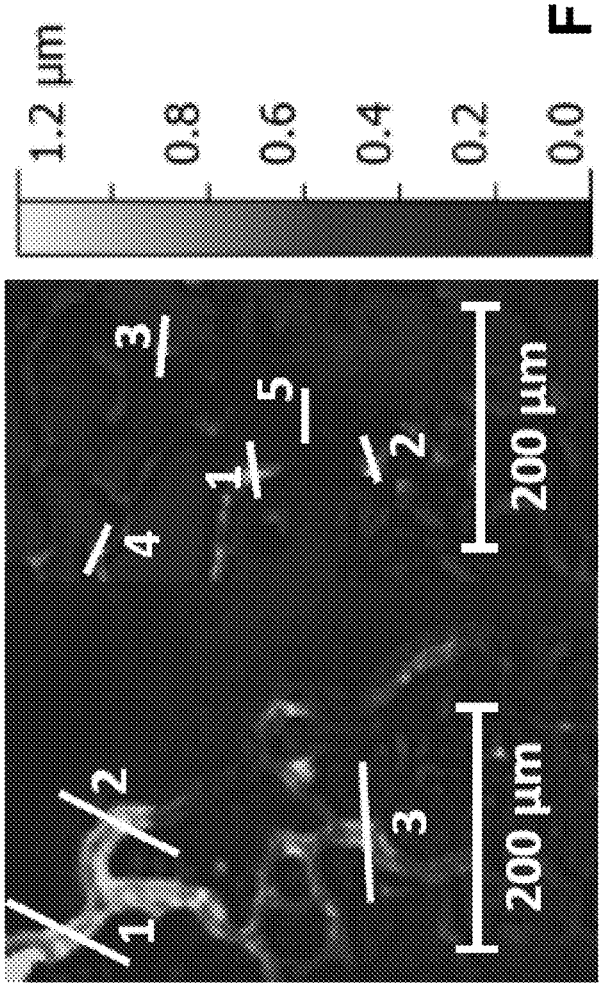
FIG. 10A is an optical profile of 1 μm polystyrene spheres on a glass cover slip.
FIG. 10B shows vertical profiles from the lines marked in the left section of the image of FIG. 10A.
FIG. 10C shows vertical profiles from the lines marked in the right section of the image of FIG. 10A.

FIG. 5 compares the manufacturer's specified diameter of the PS spheres to heights interferometrically measured with and without distortion correction through water for all particles. Diameters of micro-spheres with four diameters were measured with the method described above and after drying completely on a glass slide. The two measurements, through water and in air, are compared to the manufacturer's specified diameter, which has tolerance of ±10%. Error bars show standard deviation from four measurements. In each case the measurement through water generated values slightly higher than manufacturer's specified dry diameters—possibly because a thin layer of water persisted over the particles during measurement as shown in FIGS. 8A and 8B. The results of these validation experiments show that calculations of film thickness are accurate even for thin, non-continuous films.

These experimental results with polyimide tape and polystyrene sphere standards clearly demonstrate that this method can accurately measure organic thin films across a range of thicknesses and as low as 1 µm. Although validation was carried out with non-living solids the technique should apply to the living organic biofilm equally well because the air/water interface will assure sufficient refractive index contrast for strong fringe measurement. Applications of this method for measurement of biological thin films are discussed below.

Example 3

Flow Cell Apparatus for Interferometric Measurement of Biofilm

Biofilms often grow in environments where liquid is flowing rather than static. The development, structure, and impact of biofilms grown under flow conditions are different than for those grown under static conditions. As such, certain embodiments describe an apparatus for growing biofilms in flow conditions that is also suitable for imaging with white light interferometry.

The principle components of the flow cell apparatus are the same as the apparatus described in the Example 1. There is a microscope system, a substrate, a region for biofilm growth that can be filled with liquid, a gas bubble, and a viewing window. In the flow cell embodiment, the substrate and cover slip are enclosed at their edges, except for an inlet and outlet, which are positioned at opposite ends of the apparatus. The inlet and outlet facilitate flow of liquid media through the apparatus. In some embodiments a gas bubble may be inserted into the apparatus using a needle. In some embodiments the air bubble may be introduced at the inlet or into tubing connected to the inlet.

Figure 11:
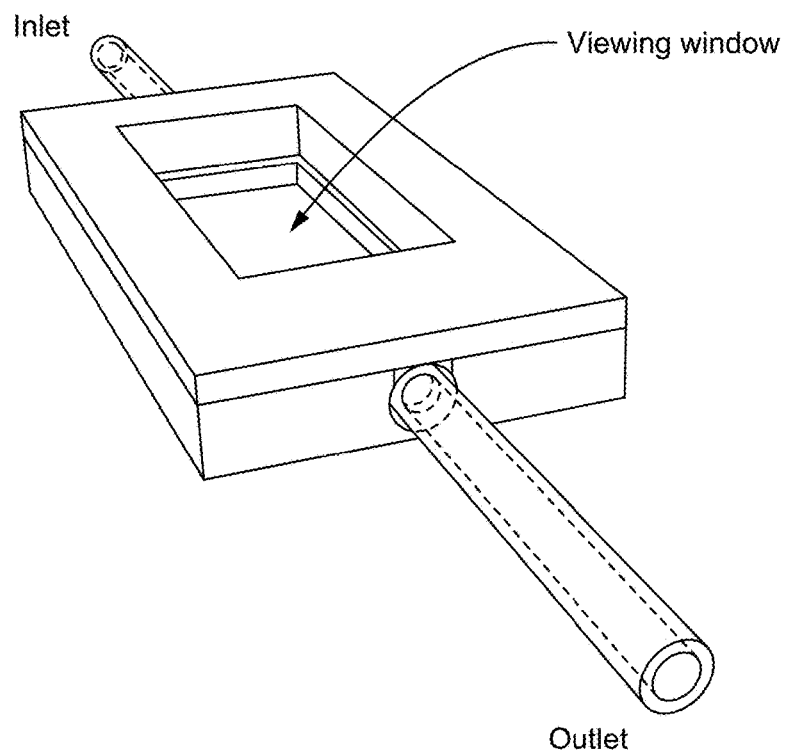
FIG. 11 is a schematic diagram of a flow cell apparatus for measuring biofilm surface properties, in accordance with one embodiment of the present invention.

FIG. 11 is a schematic diagram of a flow cell apparatus 1100 for measuring biofilm surface properties, in accordance with one embodiment of the present invention. Liquid flows from inlet 1110 to outlet 1115 and enables growth and monitoring of biofilms in a window region 1105. The substrate can be removed and replaced with desired window ports and/or growth substrates. In a typical embodiment the inlet and outlet would be connected to tubing that delivers nutrient media to and from the flow cell.

The embodiment of FIG. 11 is designed for the interferometric optical assay of live biofilms. Tubing connected to the flow cell 1100 may connect to one or more computer controlled pumps that will provide a controlled supply of nutrient media and air (essential for quantitative assay of biofilm). The flow cell 1100 will enable a broad range of surfaces and biofilms to be studied and used for its ability to support bacterial growth.

Figure 12:
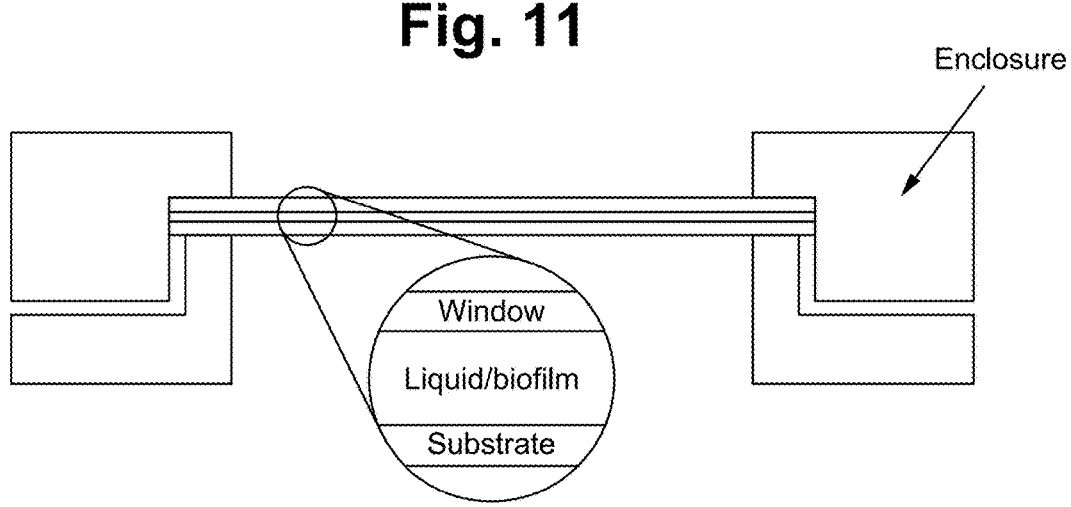
FIG. 12 is a cross-sectional view of the flow cell apparatus of FIG. 11, in accordance with one embodiment of the present invention.

FIG. 12 is a cross-sectional view of the flow cell apparatus of FIG. 11, in accordance with one embodiment of the present invention. The cross-sectional view of the flow cell apparatus shows the biofilm and surrounding liquid, grown on a substrate, with a glass window to enable imaging of the biofilm. As shown in FIG. 12, this section of the apparatus is enclosed in a casing that has an inlet and an outlet.

The casing may be made from glass, metal, polymer or plastic. No limitation is intended on the composition of the casing.

The flow cell may consist of a capillary, microchannel, or filament and may be used with or without a casing. The capillary's cross section may be square, rectangular or circular. No limitation is intended. Tubing may be connected to the ends of the capillary or may be connected with adapters. The capillary or microchannel may be part of a microfluidic device. In some embodiments of this invention the flow cell will have a septum or more than one septa, ports, or openings. These may be used to insert microorganisms, liquids and other materials into growth area of the biofilm or to remove a sample from the biofilm or liquid. In some embodiments the flow cell will be connected to a heater or incubator.

Example 4

Configuration of Flow Cell Apparatus for Automated, Multiplexed Measurements

In some embodiments, the apparatus will be configured so that parallel measurements may be made. The flow cell may have more than one flow channel and more than one viewing window. Separate inlets and outlets for each channel may be used to control flow of liquid into the channels.

Figure 13:
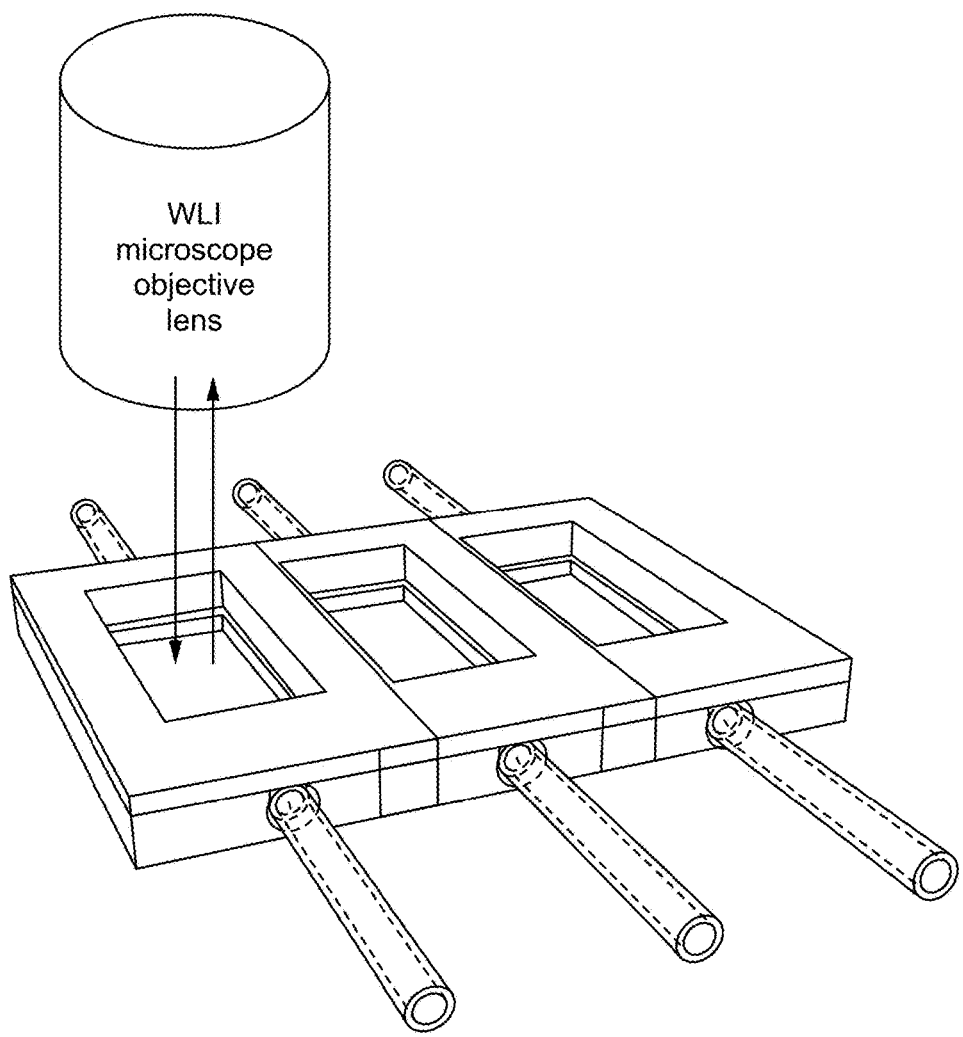
FIG. 13 is a schematic diagram of a multiplexed flow cell apparatus coupled to an objective lens of a white light interferometer (WLI), in accordance with one embodiment of the present invention.

FIG. 13 is a schematic diagram of a multiplexed flow cell apparatus coupled to an objective lens of a white light interferometer (WLI), in accordance with one embodiment of the present invention. A computer controlled microscope stage translates the flow cell plate so each well can be imaged. Computer control provides the ability for multiplexing and the potential for application of large arrays samples to be evaluated simultaneously.

A computer may also be used to control the flow of liquid in each channel. The flow may be controlled so that it is identical or so it varies between channels. Software in the computer that controls the operation of the WLI microscope may be used to move between channels and make measurements from each.

To demonstrate the apparatus described in this example, a flow cell casing was made from ABS plastic. The casing held a glass substrate and a glass cover slip (0.19 mm thickness) parallel to one another. The casing also held a needle (31G) in a position such that the needle was between the substrate and the cover slip. The needle was connected to an adapter that formed an inlet. Another adapter was placed at the opposite end of the casing and formed an outlet. The needle served to deliver liquid media to the space designated for biofilm growth. Gas bubbles were also delivered to the surface of the biofilm through this needle.

The flow cell was connected via silicone tubing to two pumps. The first pump was a peristaltic pump and the second pump was a syringe pump. The first pump connected a 1 liter reservoir of nutrient media (tryptic soy broth) reservoir to the inlet of the flow cell. The syringe pump was connected via a fine needle to a septum in the tubing just before the inlet of the flow cell. A final section of tubing connected the outlet of the flow cell to a waste reservoir.

The flow cell apparatus was placed on a micro-controlled stage of a WLI microscope. The computer connected to the microscope was used to control its operation and the operation of the stage. In some embodiments, the pumps will also be connected to a computer and controlled using software.

Figure 17:
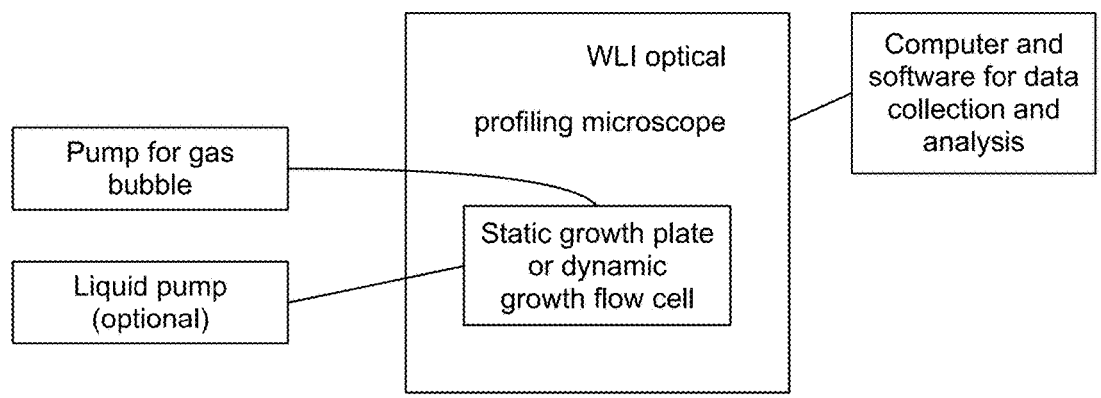
FIG. 17 is a schematic diagram showing the connection of the flow cell to pumps, with the flow cell positioned on a microscope, and the operation and function and operation of these components, including data collection and analysis, controlled using a computer and software, in accordance with one embodiment of the present invention.

FIG. 17 is a schematic diagram showing the connection of the flow cell to pumps. The schematic shows that the flow cell is positioned on the microscope. One pump may be used to supply liquid nutrient media. The other pump may be used to supply the gas bubble that is necessary for WLI measurement. The pump that supplies the gas bubble may be connected via tubing, connectors, or needles to the flow cell or to a septum, inlet, or opening. It may be connected directly to the flow cell or it may be connected in another location in the system, such as to tubing that connects to the inlet. Function and operation of these components is controlled using the connected computer.

The method of using this apparatus to measure surface topology of biofilms is described in Example 5.

This example is one embodiment of this invention and is not intending to be limiting.

Example 5

Method for Interferometric Measurement of Biofilm Using Flow Cell Apparatus

Examples 3 and 4 described flow cell apparatuses that support biofilm growth and WLI imaging. This example describes how flow cells of this invention can be used to image biofilms with WLI.

A flow cell apparatus, as described in Example 4, was placed on the stage of a WLI microscope and connected to source and waste reservoirs with silicone tubing. A peristaltic pump was used to flow TSB broth through the growth chamber contained in the flow cell (i.e. the space between the substrate and the cover glass viewing window). A concentrated culture of *Pseudomonas fluorescens* bacteria was added to the broth in the source reservoir. The flow of nutrient broth eventually spread bacteria to the growth chamber where it colonized and formed biofilm over time. At periodic intervals, the biofilm was imaged with the WLI microscope according to the method of this invention.

At the time of each measurement the peristaltic pump being used to flow broth through the flow cell was temporarily stopped. A syringe pump containing air was used to insert a small bubble into the tubing line just before the inlet to the flow cell. The air then flowed into the flow cell and formed a void between the substrate and the viewing window. Biofilm that had grown on both the substrate and the cover glass was then visible owing to the reflective air/liquid interface.

The flow cell was moved so the viewing window was in a suitable position below the interferometric objective lens of the microscope. The lens was lowered, focused, and aligned so its imaging axis was perpendicular to the viewing window. Then an imaging scan was initiated in the microscope. The objective lens was lowered through a range of approximately 500 µm. Over this range interference fringes were observed and recorded from multiple reflective interfaces. The interfaces observed were the top of the cover slip, the bottom of the cover slip, the interface of the biofilm growing on the bottom of the cover slip with the air void, the interface of the biofilm growing on the substrate with the air void, and from the surface of the substrate.

Software was used to analyze the recorded image frames, separate interference data from each surface, and reconstruct 3D profile images. The 3D profile images of the biofilm surface were of greatest interest, though the vertical position of the other interfaces was also useful for measuring biofilm thickness.

At the conclusion of data collection pumping of liquid broth to the flow cell was resumed. The flow of liquid naturally refilled the void created by the air bubble and forced the air out of the outlet of the flow cell. After a period of flow and continued growth of biofilm it was possible to capture more images from the same biofilm. The measurement process was non-destructive. Because biofilm growth was contained to within the flow cell, disruption of the biofilm by the measurement process was minimal.

Selected Examples of 3D Biofilm Images Collected Using Flow Cell Apparatus

Figure 18:
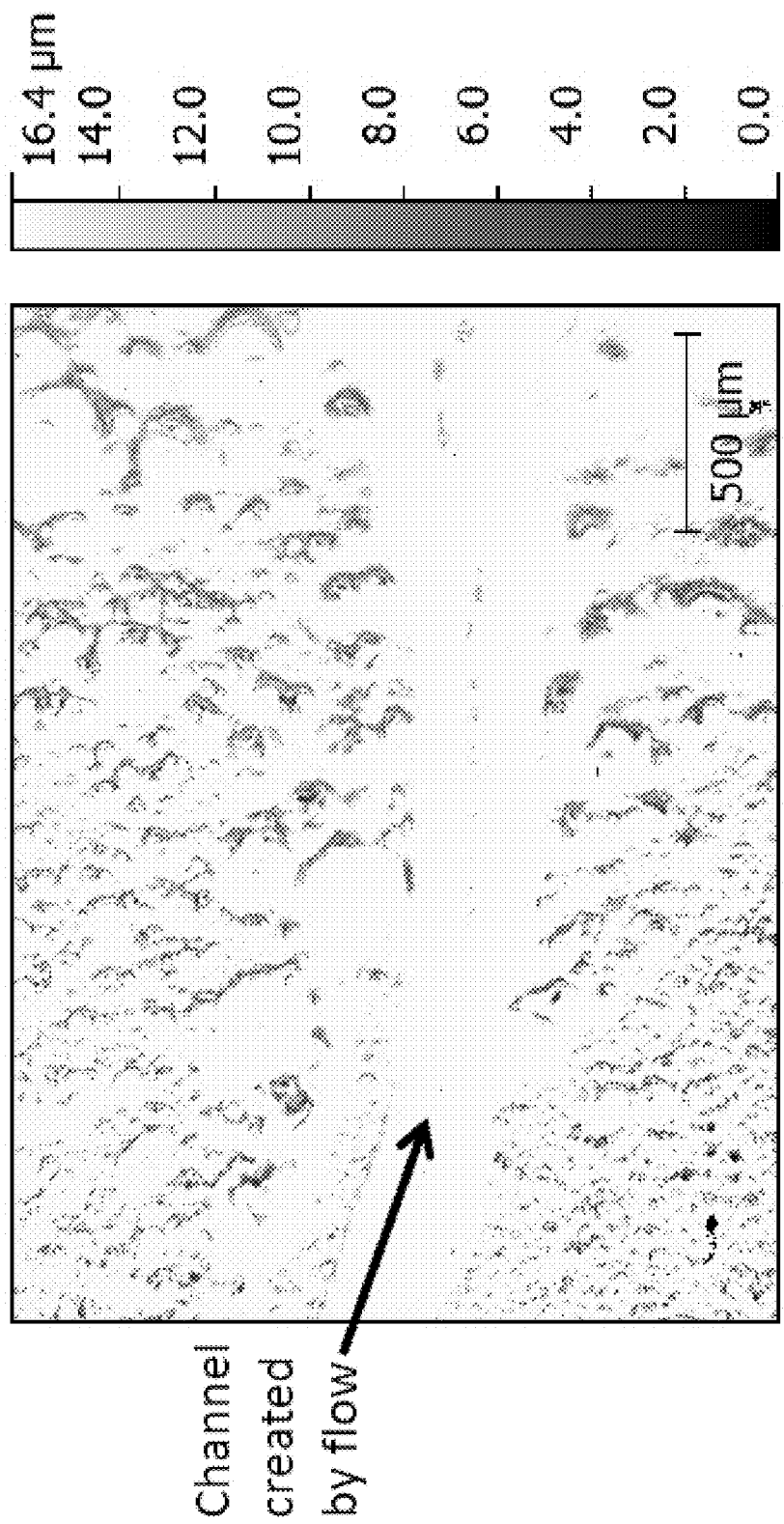
FIG. 18 is a 3D image of biofilm grown in a flow cell.

FIG. 18 is a 3D image of biofilm grown in a flow cell. The topology of the surface is indicated by the false color vertical scale shown at the right of the image. This image shows biofilm growing on the underside of the cover slip. The biofilm was effectively "hanging" from the lower surface of the cover slip when it was imaged so growth appears as depressions (darker color) from the otherwise smooth glass (lighter color). The image shows numerous individually separated colonies of bacterial biofilm. In some cases, the colonies have grown large enough that they are beginning to merge. Many of the colonies have a crescent or scalloped shape. This is likely due to the flow of nutrient broth from left to right in the image. Flow affects the shape of colonies. This example shows that WLI microscopy is a unique tool to observe this phenomenon. Another prominent feature in the image shown in FIG. 18 is the conspicuous absence of bacterial colonies in a thin channel that extends across the image from left to right. This channel is also likely a result of flowing liquid in the flow cell. The shear force of the liquid flow prevented growth of biofilm in this region.

Note that the field of view of the image in FIG. 18 is approximately 2.5 mm by 1.8 mm. This large area enables analysis of surface topology that is not as effective or accurate as with other microscopy techniques. Using this large area image it is possible to quantify surface topology of the biofilm. The root mean squared ($S_q$) roughness of the biofilm in this image is 2.07 µm as measured from a 1 by 1 mm region that excluded the channel at the center of the image. This value was calculated using 3D data visualization and analysis software.

FIG. 19 is a 3D image of a *Pseudomonas fluorescens* biofilm grown in a flow cell. In this image the biofilm has a heterogeneous and interconnected structure. At the edge of the image a segment of the image is smooth. This is not because biofilm is not present in that region. This region is beyond the edge of the air bubble so it cannot be imaged. The edge of the bubble is indicated in the figure. Topology was also quantified in this image. The root mean squared roughness of the biofilm in this image is 5.01 µm.

A principle advantage of the ability to observe biofilms non-destructively is that changes in the biofilm's structure and properties can be observed in response to changes in the local environment. One simple example of this ability is the response of the biofilm when exposed to an anti-bacterial chlorine solution.

A biofilm was grown in a flow cell for 7 days. It was periodically imaged using WLI throughout the growth phase. A final image was captured just before introduction of a 10% chlorine bleach solution. The source reservoir of nutrient broth was replaced with diluted bleach and pumped through the flow cell for 1 hour. Images of the biofilm were captured after 30 minutes and at the conclusion of the chlorine flow. Fiduciary marks on the cover slip were used to ensure that images were captured in the same location.

FIG. 20A shows an image of a biofilm of *Pseudomonas fluorescens* that was grown for 7 days. The surface is rough, indicative of strong biofilm growth. FIG. 20B shows the same location in the viewing window after 30 minutes exposure to bleach. Much of the biofilm was removed from the surface. The left part of the image is mostly clean and smooth. The right part of the image still contains some remnants of the biofilm. FIG. 20C shows the same location after 1 hour exposure to bleach. Now the surface is almost entirely smooth. Note that care was taken to ensure that flow of bleach continued at the same flow rate as nutrient broth so as not to remove biofilm by physical disruption alone. FIGS. 20A-C demonstrate that WLI imaging can be used to monitor changes in biofilm structure and topology in response to changes in the local environment. It also shows that the response to chemicals can likewise be observed. This invention could be used to study chemicals, drugs, and therapies that target biofilms. It could also be used for biomedical and environmental screening of new chemicals and materials.

This example demonstrates several key advantages of this invention. First, growing biofilm in a flow cell more closely approximates the conditions under which many biofilms grow in nature. Imaging with WLI in a flow cell enables dynamic imaging. Non-destructive imaging in the enclosed environment of the flow cell allows for continuous monitoring over time. Changes in the environment that result in changes in biofilm structure can be observed. The large area field of view enables quantification of topology and structure.

Example 6

Method and Apparatus for Interferometric Measurement of Biofilm in a Multi-well Plate This example describes a method and apparatus of observing biofilm growth in a multi-well plate using a white light interferometer. This example has the advantage of using a well-established standard tool that is commonly used in biology and biomedical research. A 96-well plate with a glass bottom was used to grow cultures of *Pseudomonas fluorescens*. The plate has a typical arrangement of 96 wells (8 rows and 12 columns) each with 5 mm inner diameter. The sides of the well and the plate's lid are made from plastic (Lucite) and the bottom of the wells is a No. 0 coverglass. No. 0 coverglass is 0.085 to 0.13 mm thick, which makes it amenable to light microscopy. The thin glass is also important for imaging with WLI. It is desirable to minimize the increase in optical path length that occurs as light passes through a medium with increased refractive index, as compared to air. The borosilicate glass cover slips used in this example have refractive index of approximately 1.52 (literature value).

To culture biofilm, *Pseudomonas fluorescens* (ATCC 13525) was cultured overnight in tryptic soy broth or TSB. Then 100 µl of the saturated culture was diluted in 5 ml of sterile TSB. The diluted culture was pipetted (100 µl) to each well. After inoculation the 96-well plate was left to grow for 5 days at room temperature. At the time of first imaging the plate's plastic cover was removed and an adhesive polyethylene film was placed over the open top of the wells. This sealed each well and prevented spilling of liquid broth when the plate was positioned for microscopy. The film served as a lid over each of the wells in the plate, as shown in FIG. 14A.

Typically, this type of plate is used with an inverted optical, confocal, or fluorescence microscope. That is, the objective lens is placed below the sample and oriented to look up. When the lenses and image sensor of the microscope are inverted the plate can remain upright during imaging. Imaging with a WLI microscope required inverting the plate instead. Inverting the plate served the important purpose of naturally positioning an air bubble adjacent to biofilm growing on the coverglass bottom of the wells. As shown in FIG. 14A the wells are partially filled with liquid broth with air headspace between the media and the plate's lid when in upright configuration.

FIG. 14A is a schematic diagram of a biofilm cultured in a well of a multi-well plate in an upright orientation. In an upright orientation of the well, an air bubble forms in the headspace above the liquid media. An air bubble cannot form adjacent to the biofilm as required for WLI imaging in upright orientation. An air bubble adjacent to the biofilm is formed by inverting the orientation of the well, as shown in FIG. 14B. In the inverted orientation, the base of the plate, which is a cover slip, becomes a viewing window for WLI biofilm imaging. The lid that covers the upright well now serves to contain liquid in the inverted well. The lid is not necessary for WLI imaging. It is only used to contain liquid from spilling. In some cases removing liquid may be desirable and the well may be inverted without a lid.

Biofilm naturally forms where liquid bacterial culture comes into contact with the walls and bottom of the inoculated wells. When inverted the biofilm will remain adhered to the surface while liquid broth and planktonic bacteria will fall into the void previous occupied by air headspace. Simultaneously, the air contained in the well forms a bubble and rises until it is in close contact with biofilm. This creates the reflective air-liquid interface that is needed for WLI imaging.

The inverted plate was placed on the stage of a WLI microscope. The objective lens was lowered until interference fringes were observed from the glass surface. The sample was then leveled using tip and tilt controls built into the microscope's stage. The objective lens was then lowered again to focus on the underside of the glass bottom (inside the well). The distance lowered is the optical thickness of the glass bottom, which is the physical thickness of the bottom multiplied by the refractive index of the glass. A 3D image was then captured by operating the WLI microscope in vertical scanning mode over a scanning range of approximately 100-200 microns. Within this scanning range light is reflected from both the flat glass well bottom and, crucially, the surface of the biofilm. When imaging of a single well was complete, the stage was translated to image biofilm in other wells.

Figure 15:
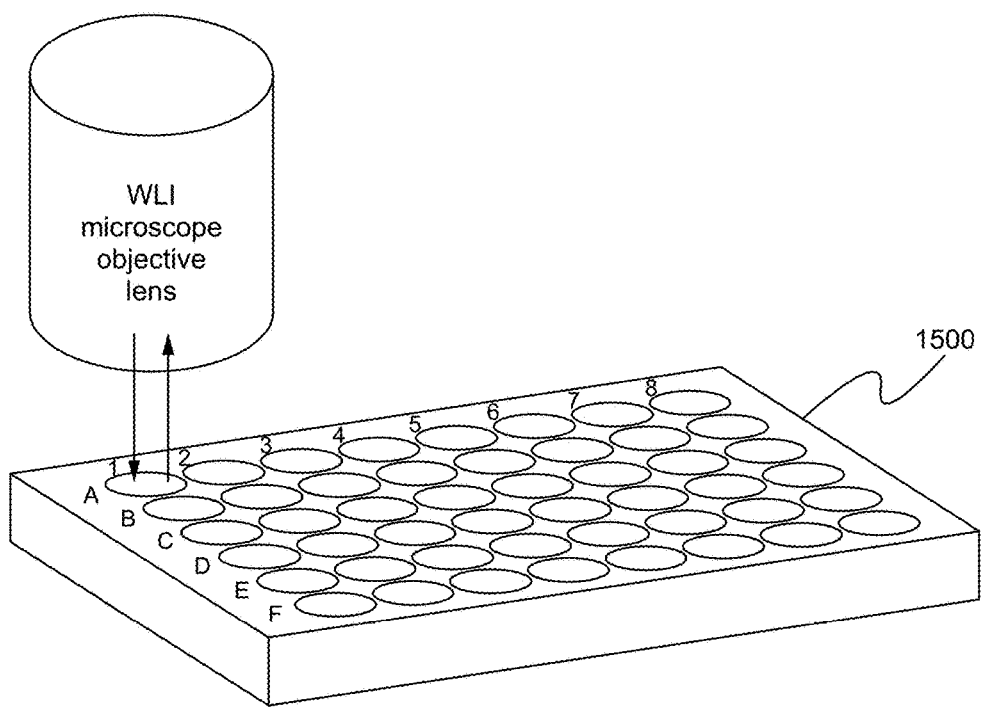
FIG. 15 is a schematic diagram of an apparatus for imaging a multi-well plate using a WLI.

FIG. 15 is a schematic diagram of an apparatus for imaging a multi-well plate 1500 using a WLI. A computer controlled microscope stage translates the multi-well plate so each well can be imaged by the microscope system. The multi-well plate is inverted for measurement.

After imaging as many wells as desired the plate was removed and gently returned to upright position. Nutrient broth returned to surround the biofilm and it was left to continue growing. Imaging of biofilms contained within the wells of the plate was non-destructive. The biofilms were imaged daily over 10 days. 3D profiles show a change in morphology of the biofilm over time. FIGS. 16A-F shows exemplary images captured from biofilms grown in a 96-well plate. In each image, color corresponds to a vertical height as shown in the color bar at right. The images show that prior to inoculation with bacteria the well was flat and smooth, as shown in FIG. 16A. When nutrient broth (TSB) was added to the wells it left some residue on the surface that makes it appear slightly textured—FIG. 16B. The peak-to-valley magnitude of this texture is approximately 500 nm, which is lower than would be expected from bacterial growth. Finally, the biofilm was imaged in wells that contained bacteria. FIGS. 16C-16F show bacteria forming colonies and structures at increasing times after inoculation with dimensions from 10-500 μm: FIG. 16C: 7 days, FIG. 16D: 8 days, FIG. 16E: 9 days, and FIG. 16F: 10 days. The development of features that are observed in one image can be followed over time The images in FIGS. 16A-16F show biofilms contained in ~1 mm circles. In fact, the biofilm likely covers the whole area of the 5 mm diameter well bottom. Meniscus effects at the walls of the well limit the imaging area. Larger imaging area can be achieved in wells with different dimensions. For example, 24-well plates have 10 mm diameter wells. For this example, biofilms of bacteria were used. It is also possible to grow biofilms of fungi, algae, diatoms and other species. More than 4000 marine species are known to adhere to surface and contribute to biofouling. This type of imaging may also be used to observe mammalian cells.

Certain cell types are difficult to grow on sterile glass or plastic surfaces. Often, a pacifying coating is applied to promote adhesion and limit toxicity. These coatings may include collagen and fibronectin. A 96-well plate was prepared with various concentrations of these surface coatings according to standard procedures that are well-known in this field. Then bacterial biofilms were grown in the coated wells. The surface coatings did not prevent or diminish the ability to image biofilms using this invention. Images of biofilm after 24 hours growth showed similar structure and development in coated wells as in uncoated wells. It will be clear from this result that coatings may also be applied in other embodiments of this invention. The application of coatings is not limited to multi-well plates.

This invention may be used with multi-well plates that have inorganic or organic coatings applied to the inside of the wells. The coatings may promote or prevent adhesion of cells. Coatings may be used to provide optical conditions that enhance data collection. Coatings may have a specific refractive index. Coatings may filter specific wavelengths of incident light. It will be clear from this result that coatings may also be applied in other embodiments of this invention.

Imaging biofilms in multi-well plates offers a unique ability to observe the macro- and micro-structure of biofilms in a self-contained and well-controlled environment. WLI microscopy can capture surface topology with high resolution, enabling study of surface roughness.

SUMMARY OF EXAMPLES

The methods described in the examples are a repeatable way to measure the surface properties of a biofilm. Since the biofilms continued to grow during repeated measurements, it can be stated with confidence that the measurement process is also fairly non-disruptive. However, other embodiments are encompassed by the methods described herein, such as using a gentler method of introduction (and removal) of the air bubble, which would reduce measurement impact on biofilm. Additionally, measurements could be made faster and less disruptive by collecting all necessary data in a single scan. This would be possible, for example, if raw fringe packet data can be separated and analyzed in parts. The methods of this invention may be used instead of traditional measures of bacterial growth like total organic carbon, cell density, cell counting, fluorescence microscopy, and confocal laser scanning microscopy.

With these optical methods it is possible to characterize topology of biofilms non-destructively over an extended growth period. The resulting profiles have very fine depth resolution with a large field of view, which enables the surface topology to be observed and the surface roughness to be measured over a large representative area. Surface roughness was observed to be an early indicator of fouling, preceding an increase in thickness by 48 hrs. The present invention will enable detailed fundamental studies of biofilm growth and will have important applications to the evaluation of anti-fouling surfaces.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. A method of measuring biofilm surface properties comprising:
   a. growing a biofilm including one or more microorganisms on a base of one or more wells of a multi-well plate containing a plurality of individual wells, each well having a base;
   b. localizing a gas bubble on a surface of the biofilm; and
   c. inverting the multi-well plate so as to position the base of the multi-well plate proximate to the objective lens of a microscope system; and
   d. capturing data of the biofilm using the microscope system to measure biofilm thickness and topology.

2. The method of claim 1 wherein the microscope system is a three-dimensional profile microscope system.

3. The method of claim 2 wherein the three-dimensional profile microscope system is a white light interferometer.

4. The method of claim 1 wherein the microscope system includes a stage to allow the multi-well plate to be inverted automatically.

* * * * *